United States Patent
Yang et al.

(10) Patent No.: US 7,410,961 B2
(45) Date of Patent: Aug. 12, 2008

(54) 2,6-DISUBSTITUTED PIPERIDDINES AS MODULATORS

(75) Inventors: Lihu Yang, Edison, NJ (US); Sander G. Mills, Scotch Plains, NJ (US); Changyou Zhou, Plainsboro, NJ (US); Stephen D. Goble, Edison, NJ (US); Alexander Pasternak, Princeton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/586,765

(22) PCT Filed: Jan. 14, 2005

(86) PCT No.: PCT/US2005/000770

§ 371 (c)(1), (2), (4) Date: Jul. 20, 2006

(87) PCT Pub. No.: WO2005/070133

PCT Pub. Date: Aug. 4, 2005

(65) Prior Publication Data

US 2007/0179158 A1    Aug. 2, 2007

Related U.S. Application Data

(60) Provisional application No. 60/537,732, filed on Jan. 20, 2004.

(51) Int. Cl.
*C07D 401/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)
*C07D 421/00* (2006.01)
*C07D 223/16* (2006.01)
*A01N 43/00* (2006.01)
*A61K 31/553* (2006.01)
*A61K 31/554* (2006.01)

(52) U.S. Cl. ............... 514/211.09; 514/339; 514/299; 514/304; 540/593; 546/268.1; 546/112; 546/125

(58) Field of Classification Search ............ 546/280.4, 546/122, 193, 113, 125, 112, 268.1; 540/597, 540/481, 580, 593; 544/224, 91, 48; 514/304, 514/299, 339, 211.09
See application file for complete search history.

(56) References Cited

U.S. PATENT DOCUMENTS

| 3,647,804 | A | 3/1972 | Rynbrandt et al. |
|---|---|---|---|
| 6,545,023 | B2 | 4/2003 | Yang et al. |
| 2002/0049222 | A1* | 4/2002 | Yang et al. ............... 514/278 |
| 2006/0069088 | A1* | 3/2006 | Goble et al. ............. 514/224.2 |
| 2006/0205761 | A1* | 9/2006 | Abbadie et al. ............ 514/300 |
| 2006/0205783 | A1* | 9/2006 | Butora et al. ............. 514/318 |
| 2006/0211722 | A1* | 9/2006 | Jiao et al. ................ 514/278 |

FOREIGN PATENT DOCUMENTS

| WO | 2004/082682 | * | 9/2004 |
|---|---|---|---|
| WO | 2004/094971 | * | 11/2004 |

OTHER PUBLICATIONS

Database CAPLUS on STN, AN 2004:802715, Jiao, et al., "Preparation of amino cycobutylamide modulators of chemokine receptor activity" abstract, WO 2004082682 A1, Sep. 30, 2004.

* cited by examiner

*Primary Examiner*—D. Margaret Seaman
*Assistant Examiner*—Niloofar Rahmani
(74) *Attorney, Agent, or Firm*—James L. McGinnis; Mark Daniel

(57) ABSTRACT

The present invention is further directed to compounds of formula (I): wherein $R^1$, $R^2$, $R^3$, $R^4$, $R^5$, $R^6$, $R^7$, $R^8$, $R^9$, $R^{10}$, $R^{16}$, $R^{17}$, $R^{18}$, $R^{19}$, $R^{20}$, $R^{21}$ and $R^{22}$ are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

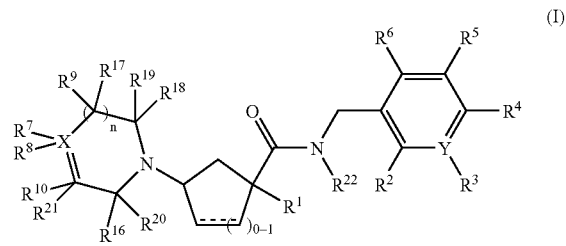

(I)

26 Claims, No Drawings

2,6-DISUBSTITUTED PIPERIDDINES AS MODULATORS

RELATED APPLICATION DATA

This is a National filing under 35 USC § 371 of PCT/US2005/000770, filed Jan. 14, 2005, which claims priority from U.S. Ser. No. 60/537,732, filed Jan. 20, 2004.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, Cytokine, 3, 165-183 (1991) and Murphy, Rev. Immun., 12, 593-633 (1994)). These molecules were originally defined by four conserved cysteines and divided into two subfamilies based on the arrangement of the first cysteine pair. In the CXC-chemokine family, which includes IL-8, GRO□, NAP-2 and IP-10, these two cysteines are separated by a single amino acid, while in the CC-chemokine family, which includes RANTES, MCP-1, MCP-2, MCP-3, MIP-1□, MIP-1β and eotaxin, these two residues are adjacent.

The □-chemokines, such as interleukin-8 (IL-8), neutrophil-activating protein-2 (NAP-2) and melanoma growth stimulatory activity protein (MGSA) are chemotactic primarily for neutrophils, whereas □-chemokines, such as RANTES, MIP-1□, MIP-1□, monocyte chemotactic protein-1 (MCP-1), MCP-2, MCP-3 and eotaxin are chemotactic for macrophages, monocytes, T-cells, eosinophils and basophils (Deng, et al., Nature, 381, 661-666 (1996)).

The chemokines are secreted by a wide variety of cell types and bind to specific G-protein coupled receptors (GPCRs) (reviewed in Horuk, Trends Pharm. Sci., 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to □-chemokines with the following characteristic pattern: CCR-1 (or "CKR-1" or "CC-CKR-1") [MIP-1□, MIP-1□, MCP-3, RANTES] (Ben-Barruch, et al., J. Biol. Chem., 270, 22123-22128 (1995); Beote, et al, Cell, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., Blood, 90, 908-928 (1997)); CCR-4 (or "CKR-4" or "CC-CKR-4") [MIP-1□ RANTES, MCP-1] (Rollins, et al., Blood, 90, 908-928 (1997)); CCR-5 (or "CKR-5" or "CC-CKR-5") [MIP-1□ RANTES, MIP-1□] (Sanson, et al., Biochemistry, 35, 3362-3367 (1996)); and the Duffy blood-group antigen [RANTES, MCP-1] (Chaudhun, et al., J. Biol. Chem., 269, 7835-7838 (1994)). The □-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., Arthritis & Rheumatism, 42, 989-992 (1999)). A review of the role of eosinophils in allergic inflammation is provided by Kita, H., et al., J. Exp. Med. 183, 2421-2426 (1996). A general review of the role of chemokines in allergic inflammation is provided by Lustger, A. D., New England J. Med., 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and Listeria monocytogenes infection (Lu et al., J. Exp. Med., 187, 601-608 (1998); Kurihara et al. J. Exp. Med., 186, 1757-1762 (1997); Boring et al. J. Clin. Invest., 100, 2552-2561 (1997); Kuziel et al. Proc. Natl. Acad. Sci., 94, 12053-12058 (1997)). Furthermore, these animals show reduced monocyte infiltration into granulomatous lesions induced by the injection of schistosomal or mycobacterial antigens (Boring et al. J. Clin. Invest., 100, et al. Am J. Path., 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/− mice backcrossed to APO-E −/−, LDL-R −/− or Apo B transgenic mice maintained on high fat diets (Boring et al. Nature, 394, 894-897 (1998); Gosling et al. J. Clin. Invest., 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds of formula I:

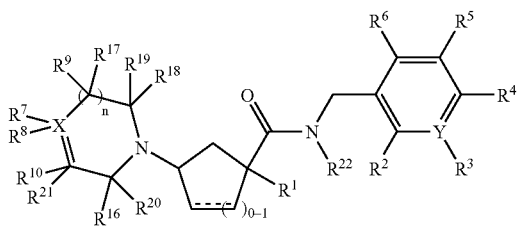

(wherein n, $R^1$, $R^2$, $R^3$, $R^4$, $R^5$, $R^6$, $R^7$, $R^8$, $R^9$, $R^{10}$, $R^{16}$, $R^{17}$, $R^{18}$, $R^{19}$, $R^{20}$, $R^{21}$, $R^{22}$, X and Y are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of Formula I:

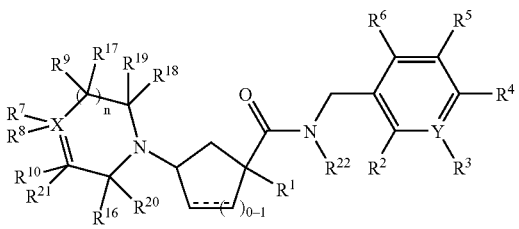

wherein:

X is C, N, O, S or $SO_2$;

Y is N or C;

$R^1$ is selected from: hydrogen, $—SO_2R^{14}$, $—C_{0-3}$alkyl-S(O)$R^{14}$, $—SO_2NR^{12}R^{12}$, $—C_{1-6}$alkyl, $—C_{0-6}$alkyl-O—$C_{1-6}$alkyl, $—C_{0-6}$alkyl-S—$C_{1-6}$alkyl, $—(C_{0-6}$alkyl)-$(C_{3-7}$cycloalkyl)-$(C_{0-6}$alkyl), hydroxy, heterocycle, —CN, $—NR^{12}R^{12}$, $—NR^{12}COR^{13}$, $—NR^{12}SO_2R^{14}$, $—COR^{11}$, $—CONR^{12}R^{12}$, and phenyl, where said alkyl and said cycloalkyl are unsubstituted or substituted with 1-7 substituents independently selected from: halo, hydroxy, —O—$C_{1-3}$alkyl, trifluoromethyl, $C_{1-3}$alkyl, —O—$C_{1-3}$alkyl, $—COR^{11}$, $—SO_2R^{14}$, $—NHCOCH_3$, $—NHSO_2CH_3$, -heterocycle, =O, —CN, where said phenyl and said heterocycle are unsubstituted or substituted with 1-3 substituents independently selected from: halo, hydroxy, $C_{1-3}$alkyl, $C_{1-3}$alkoxy and trifluoromethyl;

$R^2$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle;

$R^3$ is selected from: hydrogen, hydroxy, halo, $C_{1-3}$alkyl unsubstituted or substituted with 1-6 substituents independently selected from fluoro, hydroxy, and $—COR^{11}$, $—NR^{12}R^{12}$, $—COR^{11}$, $—CONR^{12}R^{12}$, $—NR^{12}COR^{13}$, $—OCONR^{12}R^{12}$, $—NR^{12}CONR^{12}R^{12}$, -heterocycle, —CN, $—NR^{12}—SO_2—NR^{12}R^{12}$, $—NR^{12}—SO_2—R^{14}$, $—SO^2—NR^{12}R^{12}$ and nitro, when Y is C; or $R^3$ is oxygen or is absent, when Y is N;

$R^4$ is selected from: hydrogen, $C_{1-6}$alkyl, trifluoromethyl, trifluoromethoxy, chloro, fluoro, bromo, and phenyl;

$R^5$ is selected from: $C_{1-6}$alkyl unsubstituted or substituted with one or more substituents selected from 1-6 fluoro and hydroxyl, —O—$C_{1-6}$alkyl unsubstituted or substituted with 1-6 fluoro, —CO—$C_{1-6}$alkyl unsubstituted or substituted with 1-6 fluoro, —S—$C_{1-6}$alkyl unsubstituted or substituted with 1-6 fluoro, -pyridyl unsubstituted or substituted with one or more substituents selected from halo, trifluoromethyl, $C_{1-4}$alkyl and $COR^{11}$, fluoro, chloro, bromo, $—C_{4-6}$cycloalkyl, —O—$C_{4-6}$cycloalkyl, phenyl unsubstituted or substituted with one or more substituents selected from halo, trifluoromethyl, $C_{1-4}$alkyl and $COR^{11}$, —O-phenyl unsubstituted or substituted with one or more substituents selected from halo, trifluoromethyl, $C_{1-4}$alkyl and $COR^{11}$, $—C_{3-6}$cycloalkyl unsubstituted or substituted with 1-6 fluoro, —O—$C_{3-6}$cycloalkyl unsubstituted or substituted with 1-6 fluoro, -heterocycle, —CN and $—COR^{11}$;

$R^6$ is selected from: hydrogen, $C_{1-6}$alkyl, trifluoromethyl, fluoro, chloro and bromo;

$R^7$ is nothing when X is O, S, or $SO_2$;

$R^7$ is selected from: hydrogen, $(C_{0-6}$alkyl)-phenyl, $(C_{0-6}$alkyl)-heterocycle, $(C_{0-6}$alkyl)-$C_{3-7}$cycloalkyl, $(C_{0-6}$alkyl)-$COR^{11}$, $(C_{0-6}$alkyl)-(alkene)-$COR^{11}$, $(C_{0-6}$alkyl)-$SO_3H$, $(C_{0-6}$alkyl)-W-$C_{0-4}$alkyl, $(C_{0-6}$alkyl)-$CONR^{12}$-phenyl and $(C_{0-6}$alkyl)-$CONR^{15}$—V—$COR^{11}$, when X is C or N, where V is selected from $C_{1-6}$alkyl or phenyl, where W is selected from: a single bond, —O—, —S—, —SO—, $—SO_2—$, —CO—, $—CO_2—$, $—CONR^{12}—$ and $—NR^{12}—$, where said $C_{0-6}$alkyl is unsubstituted or substituted with 1-5 substituents independently selected from: halo, hydroxy, $—C_{0-6}$alkyl, —O—$C_{1-3}$alkyl, trifluoromethyl and $—C_{0-2}$alkyl-phenyl, where said alkene is unsubstituted or substituted with 1-3 substituents independently selected from: halo, trifluoromethyl, $C_{1-3}$alkyl, phenyl and heterocycle;

where said phenyl, heterocycle, cycloalkyl and $C_{0-4}$alkyl are independently unsubstituted or substituted with 1-5 substituents independently selected from: halo, trifluoromethyl, hydroxy, $C_{1-6}$alkyl, —O—$C_{1-3}$alkyl, $—C_{0-3}—COR^{11}$, —CN, $—NR^{12}R^{12}$, $—CONR^{12}R^{12}$ and $—C_{0-3}$-heterocycle, or where said phenyl and heterocycle are fused to another heterocycle, which itself may be unsubstituted or substituted with 1-2 substituents independently selected from hydroxy, halo, $—COR^{11}$, and $—C_{1-4}$alkyl;

$R^8$ is selected from: hydrogen, hydroxy, $C_{1-6}$alkyl, $C_{1-6}$alkyl-hydroxy, —O—$C_{1-3}$alkyl, $—COR^{11}$, $—CONR^{12}R^{12}$ and —CN, when X is C, or;

$R^8$ is nothing when X is O, S, $SO_2$ or N, or when a double bond joins the carbons to which $R^7$ and $R^{10}$ are attached;

or $R^7$ and $R^8$ are joined together to form a ring which is selected from: 1H-indene, 2,3-dihydro-1H-indene, 2,3-dihydro-benzofuran, 1,3-dihydro-isobenzofuran, 2,3-dihydro-benzothiofuran, 1,3-dihydro-isobenzothiofuran, 6H-cyclopenta[d]isoxazol-3-ol, cyclopentane and cyclohexane, where said ring is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle;

$R^9$ and $R^{10}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, =O when $R^9$ or $R^{10}$ is connected to the ring via a double bond and halo;

or $R^7$ and $R^9$, or $R^8$ and $R^{10}$, are joined together to form a ring which is phenyl or heterocycle, where said ring is unsubstituted or substituted with 1-7 substituents independently selected from: halo, trifluoromethyl, hydroxy, $C_{1-3}$alkyl, —O—$C_{1-3}$alkyl, —$COR^{11}$, —CN, —$NR^{12}R^{12}$ and —$CONR^{12}R^{12}$;

$R^{11}$ is independently selected from: hydroxy, hydrogen, $C_{1-6}$ alkyl, —O—$C_{1-6}$alkyl, benzyl, phenyl, $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{12}$ is selected from: hydrogen, $C_{1-6}$ alkyl, benzyl, phenyl and $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{13}$ is selected from: hydrogen, $C_{1-6}$ alkyl, —O—$C_{1-6}$alkyl, benzyl, phenyl and $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{14}$ is selected from: hydroxy, $C_{1-6}$ alkyl, —O—$C_{1-6}$alkyl, benzyl, phenyl and $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{15}$ is hydrogen or $C_{1-4}$alkyl, or $R^{15}$ is joined via a 1-5 carbon tether to one of the carbons of V to form a ring;

$R^{17}$, $R^{19}$, $R^{20}$ and $R^{21}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, trifluoromethyl and halo;

$R^{16}$ and $R^{18}$ are independently selected from: hydroxy, $C_{1-6}$alkyl, $C_{1-6}$alkyl-$COR^{11}$, $C_{1-6}$alkyl-hydroxy, —O—$C_{1-3}$alkyl and halo, where said alkyl is unsubstituted or substituted with 1-6 substituents independently selected from fluoro and hydroxyl;

or $R^{16}$ and $R^{18}$ together form a bridge consisting of —$C_{1-4}$alkyl-, —$C_{0-2}$alkyl-O—$C_{1-3}$alkyl- or —$C_{1-3}$alkyl-O—$C_{0-2}$alkyl-, where said alkyl is unsubstituted or substituted with 1-2 substituents independently selected from oxy (where the oxygen is joined to the bridge via a double bond), fluoro, hydroxy, methoxy, methyl and trifluoromethyl;

$R^{22}$ selected from: hydrogen, phenyl, $C_{1-6}$alkyl which is substituted or unsubstituted with 1-6 substituents selected from: —$COR^{11}$, hydroxy, fluoro, chloro and —O—$C_{1-3}$ alkyl;

or $R^2$ and $R^{22}$ together are a linker forming a heterocycle ring, said linker selected from (with the left side of the linker being bonded to the amide nitrogen at $R^{22}$): —$CH_2$—$(CR^{23}R^{23})_{1-3}$—, —$CH_2$—$NR^{24}$—, —$NR^{12}$—$CR^{23}R^{23}$—, —$CH_2O$—, —$CH_2SO_2$—, —$CH_2SO$—, —$CH_2S$—, —$CR^{23}R^{23}$—;

$R^{23}$ is independently selected from: hydrogen, $C_{1-3}$alkyl unsubstituted or substituted with 1-6 substituents independently selected from fluoro and hydroxy, $COR^{13}$, $SO_2R^{14}$, $SO_2NR^{12}R^{12}$, hydroxy, halo, —$NR^{12}R^{12}$, —$COR^{11}$, —$CONR^{12}R^{12}$, —$NR^{12}COR^{13}$, —$OCONR^{12}R^{12}$, —$NR^{12}CONR^{12}R^{12}$, -heterocycle, —CN, —$NR^{12}$—$SO_2$—$NR^{12}R^{12}$, —$NR^{12}$—$SO_2$—$R^{14}$, —$SO_2$—$NR^{12}R^{12}$;

or one $R^{23}$ is =O and the other $R^{23}$ is absent;

where $R^{24}$ is selected from: hydrogen, $C_{1-3}$alkyl where said alkyl is unsubstituted or substituted with 1-6 substituents independently selected from fluoro and hydroxy, $COR^{13}$, $SO_2R^{14}$ and $SO_2NR^{12}R^{12}$;

n is selected from 0, 1 and 2;

the dashed line represents an optional bond;

and pharmaceutically acceptable salts thereof and individual diastereomers thereof.

Another embodiment of the present invention includes compounds of Formula I, wherein $R^{16}$ and $R^{18}$ together form a bridge consisting of —$C_{1-4}$alkyl-, —$C_{0-2}$alkyl-O—$C_{1-3}$alkyl- or —$C_{1-3}$alkyl-O—$C_{0-2}$alkyl-, where said alkyl is unsubstituted or substituted with 1-2 substituents independently selected from: oxy where the oxygen is joined to said bridge via a double bond, fluoro, hydroxy, methoxy, methyl and trifluoromethyl.

Another embodiment of the present invention includes compounds of Formula Ia:

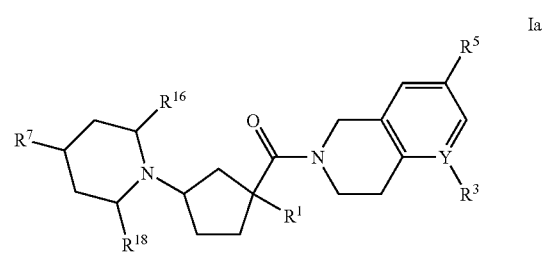

Ia wherein $R^1$, $R^3$, $R^5$, $R^7$, $R^{16}$, $R^{18}$, and Y, are as defined above, and pharmaceutically acceptable salts thereof and individual diastereomers thereof.

Another embodiment of the present invention includes compounds of Formula Ib:

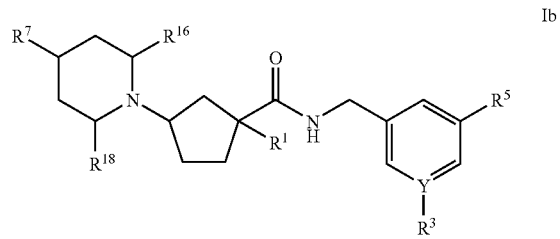

Ib wherein $R^1$, $R^3$, $R^5$, $R^7$, $R^{16}$, $R^{18}$, and Y are as defined above, and pharmaceutically acceptable salts thereof and individual diastereomers thereof.

Another embodiment of the present invention includes compounds of Formula Ic:

Ic wherein $R^1$, $R^3$, $R^5$, $R^7$, and Y, are as defined above, and pharmaceutically acceptable salts thereof and individual diastereomers thereof.

Another embodiment of the present invention includes compounds of Formula Id:

Id wherein $R^1$, $R^3$, $R^5$, $R^7$, and Y are as defined above, and pharmaceutically acceptable salts thereof and individual diastereomers thereof.

In another aspect of the present invention $R^1$ is $C_{1-6}$alkyl, unsubstituted or substituted with hydroxyl or 1-6 fluoro.

In a still further aspect of the present invention $R^1$ is selected from: —CH(CH$_3$)$_2$, —CH(OH)CH$_3$ and —CH$_2$CF$_3$.

In another aspect of the present invention $R^2$ is hydrogen.

In another aspect of the present invention $R^2$ is connected to $R^{22}$ by —CH$_2$—CH$_2$—.

In a still further aspect of the present invention when Y is N, $R^3$ is absent.

In a further aspect of the present invention when Y is N, $R^3$ is O (to give a N-oxide).

In a still further aspect of the present invention when Y is C, $R^3$ is selected from: hydrogen, halo, hydroxyl, $C_{1-3}$alkyl where said alkyl is unsubstituted or substituted with 1-6 substituents independently selected from fluoro and hydroxy, —COR$^{11}$, —CONR$^{12}$R$^{12}$, -heterocycle, —NR$^{12}$—SO$_2$—NR$^{12}$R$^{12}$, —NR$^{12}$—SO$_2$—R$^{14}$, —SO$_2$—NR$^{12}$R$^{12}$, -nitro and —NR$^{12}$R$^{12}$.

In another aspect of the present invention when Y is C, $R^3$ is hydrogen, fluoro, or trifluoromethyl.

In another aspect of the present invention $R^4$ is hydrogen.

In another aspect of the present invention $R^5$ is selected from: $C_{1-6}$alkyl substituted with 1-6 fluoro, —O—$C_{1-6}$alkyl substituted with 1-6 fluoro, chloro, bromo and phenyl.

In another aspect of the present invention $R^5$ is trifluoromethyl.

In another aspect of the present invention $R^6$ is hydrogen.

In another aspect of the present invention $R^7$ is phenyl, heterocycle, $C_{3-7}$cycloalkyl, $C_{1-6}$alkyl, —COR$^{11}$ or —CONH-V-COR$^{11}$, where V is $C_{1-6}$alkyl or phenyl, where said phenyl, heterocycle, $C_{3-7}$cycloalkyl and $C_{1-6}$alkyl are unsubstituted or substituted with 1-5 substituents independently selected from: halo, trifluoromethyl, hydroxy, $C_{1-3}$alkyl, —O—$C_{1-3}$alkyl, —COR$^{11}$, —CN, -heterocycle and —CONR$^{12}$R$^{12}$.

In still another aspect of the present invention, when X is not O, $R^7$ is phenyl, heterocycle, $C_{1-4}$alkyl, —COR$^{11}$, and —CONH-V-COR$^{11}$, where V is selected from $C_{1-6}$alkyl or phenyl, and where the phenyl, heterocycle, and $C_{1-4}$alkyl is unsubstituted or substituted with 1-3 substituents independently selected from: halo, hydroxy, $C_{1-3}$alkyl, —O—$C_{1-3}$alkyl, —COR$^{11}$ and heterocycle.

In still another aspect of the present invention, when X is C, $R^7$ is selected from:

| | | | |
|---|---|---|---|
| (a) | [tetrazole] | (j) | [imidazole] |
| (b) | para-fluorophenyl, | (k) | [pyrimidine] |
| (c) | 3-carboxyphenyl, | (l) | [pyrazole] |
| (d) | 3-carboxy-4-fluorophenyl, | (m) | [thiadiazolone] |
| (e) | phenyl, | (n) | [triazole] |
| (f) | —CO$_2$CH$_2$CH$_3$, | (o) | [triazole] |
| (g) | —CO$_2$H | (p) | [tetrazole] |
| (h) | —CONHCH$_3$ | (q) | [isopropyl triazole] |

| (i) | -hydroxy | (r) | 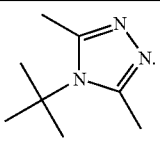 |

In another aspect of the present invention, when X is C, $R^8$ is hydrogen.

In another aspect of the present invention $R^9$ and $R^{10}$ are hydrogen.

In another aspect of the present invention $R^{16}$ is selected from: methyl, fluoro and trifluoromethyl.

In one aspect of the current invention $R^{17}$ is hydrogen.

In another aspect of the current invention $R^{18}$ is selected from: methyl, fluoro and trifluoromethyl.

In another aspect of the present invention $R^{16}$ and $R^{18}$ are joined by —$CH_2$—$CH_2$— to make a 5 membered heterocycle.

In one aspect of the current invention $R^{19}$ is hydrogen.
In one aspect of the current invention $R^{20}$ is hydrogen.
In one aspect of the current invention $R^{21}$ is hydrogen.
In one aspect of the current invention $R^{22}$ is hydrogen.

In another aspect of the current invention $R^{22}$ and $R^2$ together are a linker which is —$CH_2$—$CH_2$—.

In yet another aspect of the present invention n=1.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo.

As used herein, "alkyl" is intended to mean linear, branched and cyclic carbon structures having no double or triple bonds. $C_{1-8}$, as in $C_{1-8}$alkyl, is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. More broadly, $C_{a-b}$alkyl (where a and b represent whole numbers) is defined to identify the group as having a through b carbons in a linear or branched arrangement. $C_0$, as in $C_0$alkyl is defined to identify the presence of a direct covalent bond. "Cycloalkyl" is an alkyl, part or all of which forms a ring of three or more atoms.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are employed. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 ☐M Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 ☐l). Monocytes (150,000 cells) were added to the topside of the filter (30 ☐l) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 ☐M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a certain embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases, and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fascitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomniasis, Clonorchiasis), cestodes (tape worms) (Echinococcosis, Taeniasis saginata, Cysticercosis), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as □□-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolinetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HM:G-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), □-glucosidase inhibitors (acarbose) and glitazones (troglitazone and pioglitazone); (l) preparations of interferon beta (interferon beta-1□, interferon beta-1□); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.01 to 500 mg per kg patient body weight per day which can be administered in single or multiple doses. In certain embodiments the dosage level will be about 0.1 to about 250 mg/kg per day; or from about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, or 2.0 to 500, or 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are commercially available, made by known procedures, or prepared as illustrated herein.

One of the principal routes used for preparation of compounds within the scope of the instant invention which bear a 1,1,3-trisubstituted cyclopentane framework 1-5 is depicted in Scheme 1A. According to this route, keto acids 1-1 (Schemes 2) is coupled to amines 1-2 (Schemes 3). This can be accomplished in various ways, including by first converting the acid to its acid chloride with a reagent such as oxalyl chloride, and then combining with amine 1-2 in the presence of a base such as triethylamine. Reductive amination of 1-3 with an amine 1-4 using, for example, $NaB(OAc)_3H$ or $NaBH_3CN$ as the reducing agent gives chemokine receptor modulators 1-5. The compounds 1-5, which can be synthesized according to the chemistry described in Scheme 1 represent stereoisomeric mixtures (Eliel, E. E., Wilen, S. H., *Stereochemistry of Organic Compounds*, John Wiley & Sons, Inc., New York). In particular, compounds 1-5 are often obtained as a mixture of cis and trans isomers. When 1-1 is a single stereoisomer (1-1a) only 2 possible isomers of 1-5 can result (cis and trans); these can be separated by a variety of methods, including by preparative TLC, flash chromatography, MPLC, or by HPLC using a column with a chiral stationary phase. When 1-1 is racemic, a total of 4 possible isomers of 1-5 can be obtained. Again, these may be separated by HPLC using a column with a chiral stationary phase, or by a combination of the methods above. The synthesis of racemic 1-1 is detailed in Scheme 2A, while syntheses of the chiral 1-1a is described in Schemes 2B.

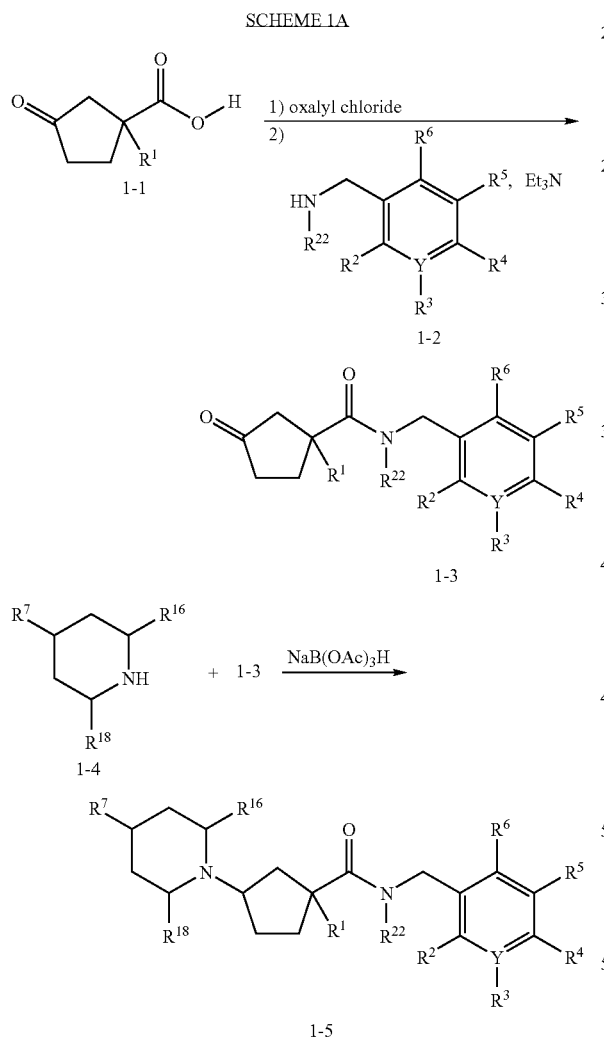

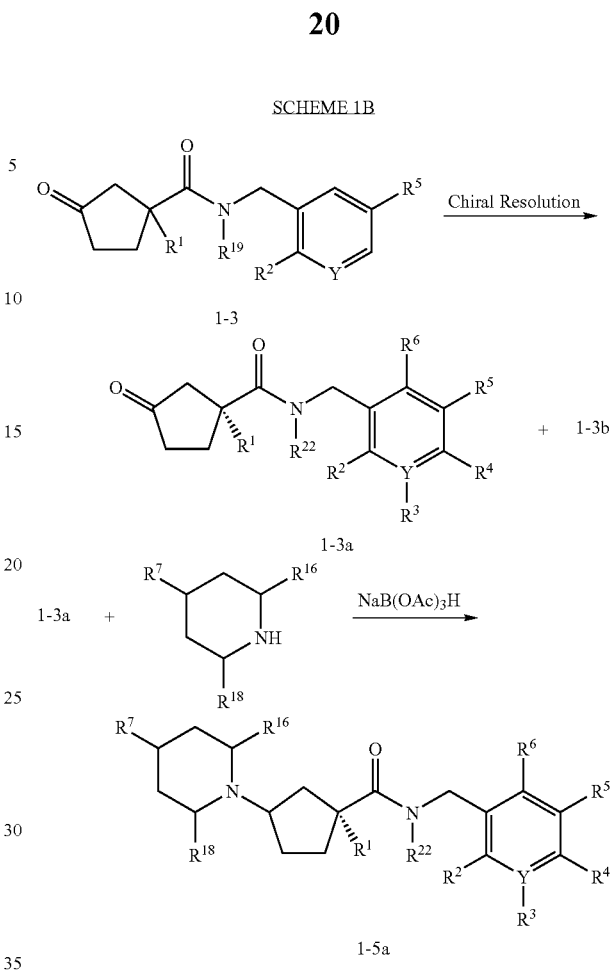

Keto amide 1-3 can also be resolved into its individual stereoisomers before the reductive amination step as shown in Scheme 1B. If the amine 1-2 and the amine 1-4 are achiral, 1-3 is resolved into its individual enantiomers (1-3a and 1-3b). After the reductive amination step, a mixture of diastereomers would result (1-5a and 1-5b), which could be further resolved.

One of the principal routes used for preparation of Intermediate 1-1 is outlined in Scheme 2A. According to this route, 3-oxocyclopentanecarboxylic acid (2-1), which can be synthesized following a known procedure (Stetter, H., Kuhlman, H., *Liebigs Ann. Chim.*, 1979, 944) is esterified under standard conditions. When $R^{18}$ represents a tert-Butyl group, the respective ester 1-6 can be prepared by reacting the appropriate alcohol, in this case tert-butanol, with acid 2-1 in the presence of sulfuric acid. Protection of the oxo-group in 2-1 can be achieved by a number of ways (Greene, T., Wuts, P. G. M., *Protective Groups in Organic Chemistry*, John Wiley & Sons, Inc., New York, N.Y. 1991). The particularly suitable dimethyl acetal protecting group can be introduced using trimethyl orthoformate as a reagent in a suitable solvent such as dichloromethane and methyl alcohol in the presence of an acidic catalyst. Alternatively, in the case of $R^{18}$ being a methyl group, the acid 2-1 can be converted to 2-3 directly by using trimethyl orthoformate and an acidic catalyst, such as para-toluenesulfonic acid. An alkylation of esters 2-3 with an alkylating agent such as an alkyl chloride, bromide or iodide in the presence of an appropriate base such as lithium diisopropylamide, produces intermediates 2-4. The ester protecting group present in 2-4 can be removed in a number of ways, depending on the nature of the ester. Methyl esters ($R^{18}$=methyl) can be hydrolyzed in the presence of an acid or base at ambient or elevated temperatures, whereas tert-butyl esters ($R^{18}$=tert-butyl) can be easily cleaved under acidic conditions. Under these conditions, the dimethyl acetal is simultaneously deprotected to give 1-1.

SCHEME 2A

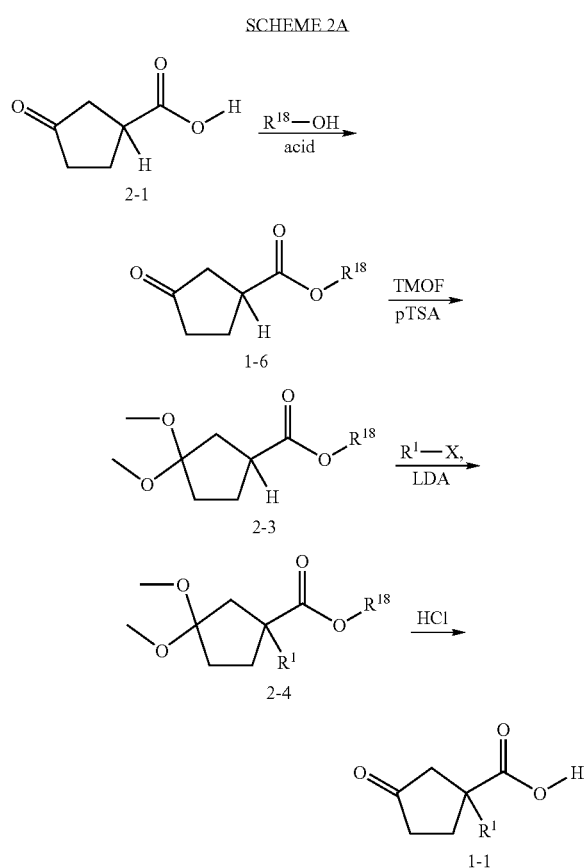

Intermediate 1-1 can be prepared as a single stereoisomer (1-1a) in various ways including by the route depicted in Scheme 2B. According to Scheme 2B, racemic 1-1 can be converted to its benzyl ester. There are many ways to effect this esterification, one of which being by a sequence involving conversion to the corresponding acid chloride with, for example oxalyl chloride, followed by treatment with benzyl alcohol in the presence of a base such as triethylamine. Then the racemic benzyl ester 2-5 can be separated by chiral preparative HPLC to give 2-5a as a single stereoisomer. Removal of the benzyl group to give the chiral ketoacid 1-1a can be accomplished in several ways. One convenient way is by hydrogenolysis in the presence of a catalyst such as Pd/C.

SCHEME 2B

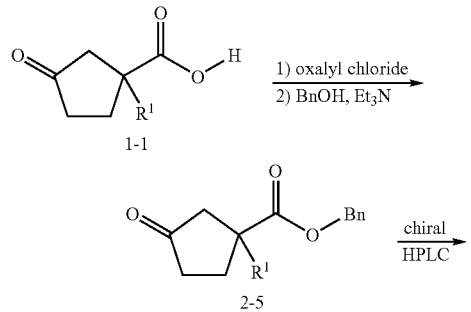

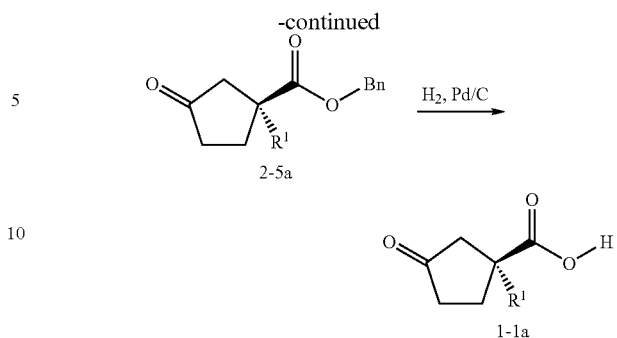

Amines 1-2 are either commercially available or prepared according to literature procedures or as shown in schemes 3A and 3B. The 5-aza-tetrahydroisoquinoline fragment can be prepared in accordance to the literature methods of MarCoux, J-F. et al. (*J. Chem. Lett.,* 2000, 2 (15), 2339-2341). Alternatively, it can be prepared as outlined in Scheme 3A. Compound 3-1, normally obtained from commercial sources, is brominated (Br$_2$, AcOH) to give 3-2. Metal halogen exchange (NaH, t-butyl lithium) followed by treatment with DMF provides aldehyde 3-3. Conversion of the aldehyde group to a nitrile can be achieved with sodium formate, hydroxylamine hydrochloride and formic acid. The resulting nitrile 3-4 can be treated with phosphorous oxychloride to give 2-chloropyridine 3-5. Displacement of the chloro group can be achieved with the sodium salt of a dialkylmalonate. Reduction of the nitrile group of 3-6 with hydrogen and Raney Ni catalyst is accompanied by cyclization to afford compound 3-7. Decarboxylation can be achieved in a variety of ways depending on the ester. In the case represented in Scheme 3A, the t-butyl ester was decarboxylated with TFA to give 3-8. Reduction (BH$_3$), followed by protection of the resulting amine using Boc$_2$O, gives 3-9, which can be conveniently purified. Removal of the Boc protecting group to give 1-2a can be achieved in various ways, including by treatment with anhydrous HCl in dioxane or some other solvent.

SCHEME 3A

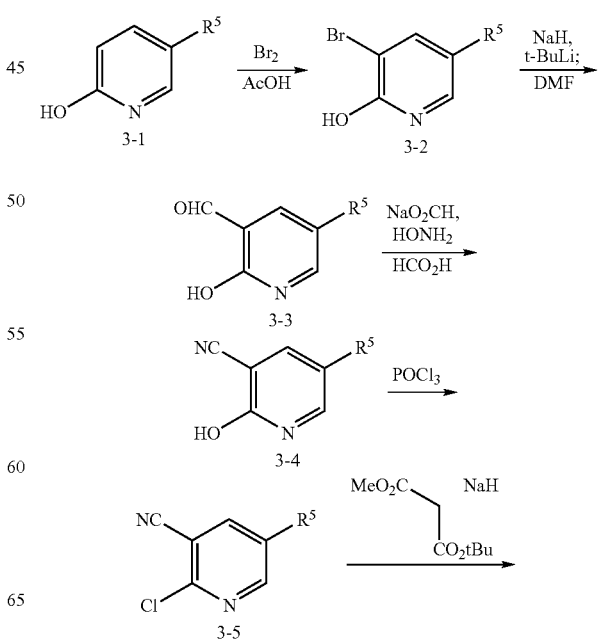

-continued

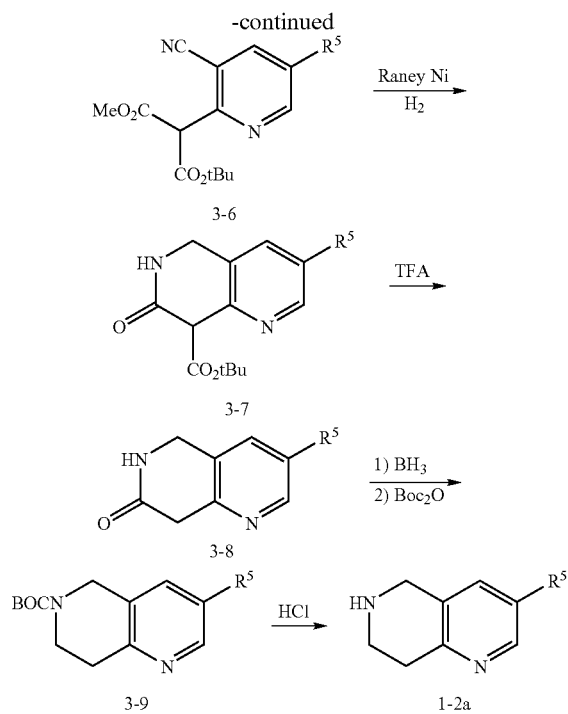

The simple tetrahydroisoquinoline (1-2b) is depicted in Scheme 3B. According to this, the commercially available 4-trifluoromethyl phenylacetonitrile (3-23) is converted to the corresponding amine (3-24) using hydrogenation in the presence of Ra—Ni, and trifluoroacetic anhydride is then used to cap the amine. The resultant amide (3-25) is treated with formaldehyde in the presence of sulfuric acid to give the cyclic compound (3-26) which is further converted into tetrahydroisoquinoline (1-2b).

SCHEME 3B

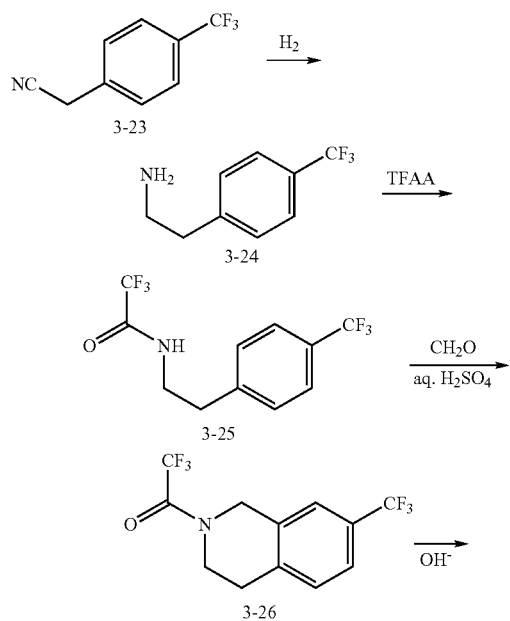

-continued

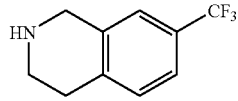

1-2b

Amines 1-4 where synthesized according to literature procedures. In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). MPLC refers to medium pressure liquid chromatography and was carried out on a silica gel stationary phase unless otherwise noted. NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative procedures for the preparation of the compounds used in the following Examples or which can be substituted for the compounds used in the following Examples which may not be commercially available.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). NMR spectra were obtained in $CDCl_3$ solution unless otherwise noted. Coupling constants (I) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

In some cases the order of carrying out the foregoing reaction schemes may be varied to facilitate the reaction or to avoid unwanted reaction products.

The following are representative procedures for the preparation of the compounds used in the following Examples or which can be substituted for the compounds used in the following Examples which may not be commercially available.

INTERMEDIATE 1

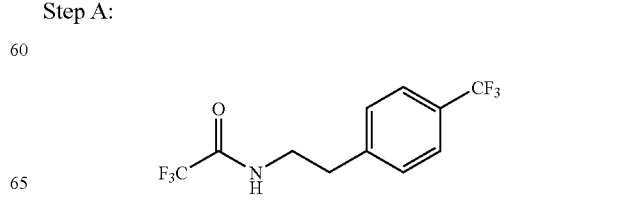

Step A:

A solution of 4-trifluoromethylphenylacetonitrile (10 g, 49 mmol) in a mixture of ethanol (100 mL) and ammonium hydroxide (20 mL of a 29.3% aqueous solution) was hydrogenated over Raney nickel (1 g) for 16 h. The catalyst was removed by filtration through celite and the filtrate evaporated to dryness. The neat residue was added in a dropwise manner to trifluoroacetic anhydride (25 mL, 180 mmol) cooled at 0° C. and the resulting mixture stirred at 0° C. for 30 minutes. The reaction mixture was poured onto ice (250 mL) and the resulting mixture stirred for 30 minutes after which the precipitate was removed by filtration and air dried to give the product as a white solid (13.4 g, 90%).

Step B:

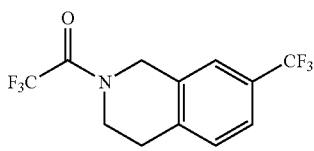

To a mixture of the product from step A (13.4 g, 44.0 mmol) and paraformaldehyde (2 g, 50 mmol) was added in one portion a mixture of concentrated sulfuric acid (90 mL) and glacial acetic acid (60 mL) and the resulting mixture stirred at room temperature for 16 hours. The reaction mixture was poured onto a mixture of ice and water (1 L) and extracted with ethyl acetate (3×150 mL); the combined ethyl acetate layers were washed with water (3×500 mL), saturated NaHCO$_3$ (200 mL), and sat NaCl (100 mL), dried over MgSO$_4$, filtered and evaporated in vacuo. The residue was purified by column chromatography on silica elution with 10% Et$_2$O in hexanes to give the product (8.29 g, 60%).

Step C:

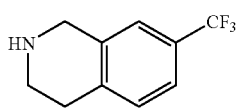

To a solution of the trifluoroacetamide formed in Step B (8.29 g, 26.0 mmol) in ethanol (200 mL) was added a solution of potassium carbonate (20 g, 150 mmol) in water (50 mL), and the resulting mixture stirred at reflux for 1 hour. The ethanol was removed by rotary evaporation and water (150 mL) was added to the residue. Extracted with CH$_2$Cl$_2$ (3×100 mL), the combined CH$_2$Cl$_2$ layers were washed with sat NaCl (100 mL), dried over Na$_2$SO$_4$, filtered and evaporated in vacuo to give the product (5.2 g, 91%); $^1$H NMR 500 MHz (CDCl$_3$) δ=1.81 (1H, br s), 2.84 (2H, d, J=6.0 Hz), 3.15 (2H, t, J=6.0 Hz), 4.05 (2H, s), 7.19 (1H, d, J=8.0 Hz), 7.27 (1H, s), 7.37 (1H, d, J=8.0 Hz).

INTERMEDIATE 2

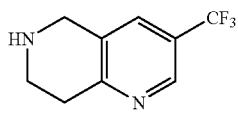

Step A:

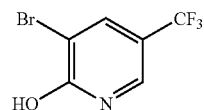

To a solution of 5-trifluoromethyl-2-pyridinol (51.0 g, 307 mmol) and sodium acetate (26.2 g, 319 mmol) in glacial acetic acid (200 mL) was added bromine (16.7 mL, 325 mmol) and the resulting mixture was heated at 80° C. for 2.5 hours. The reaction was allow to cool to room temperature and then was evaporated under reduced pressure. The residue was neutralized with saturated NaHCO$_3$ solution and extracted with ethyl acetate (3×200 mL). The organic layers were combined, dried over MgSO$_4$, filtered, and evaporated in vacuo to yield 74.45 g (98.7%) of the crude product. $^1$H NMR (400 MHz, CDCl$_3$) δ 8.04 (d, J=2.6 Hz, 1H), 7.89 (m, 1H).

Step B:

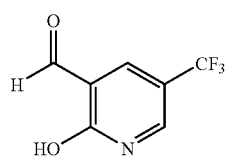

Under nitrogen, the substituted pyridine, described in Step A (48.8 g, 202 mmol) was added by small portions to a suspension of NaH (8.9 g, 220 mmol) in anhydrous THF (500 mL). After complete addition of the intermediate, the reaction mixture was cooled to −78° C. and treated with tert-butyl-lithium (260 mL, 444 mmol) added dropwise via syringe. After stirring for 5 minutes, DMF (50 mL, 707 mmol) was added slowly to maintain the temperature below −50° C. The resulting mixture was then stirred for 10 hours allowing to warm to room temperature. The mixture was quenched with 2N HCl and then diluted with ethyl acetate (1000 mL). The organic layer was separated, washed with brine, dried over MgSO4, and evaporated in vacuo. The desired product was precipitated out of ethyl acetate and hexane and filtered to yield a light brown solid (28.55 g, 73.8%). $^1$H NMR (500 MHz, CD$_3$OD) δ 10.13 (s, 1H), 8.21 (s, 2H).

Step C:

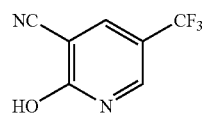

A mixture of the intermediate from Step B (18 g, 95 mmol), sodium formate (7.1 g, 105 mmol), hydroxylamine hydrochloride (7.3 g, 110 mmol), and formic acid (150 mL) was stirred at room temperature for 2 hours and then refluxed overnight. The reaction mixture was cooled and let stand at room temperature for 7 days. The reaction was poured into water and extracted with ethyl acetate (3×). Combined organic layers were washed with water (2×), saturated NaHCO$_3$ and brine, dried over Na$_2$SO$_4$, filtered, and concentrated in vacuo to yield the desired product as a brown powder (17.84 g, 89.8%). ¹H NMR (400 MHz, CD₃OD) δ 8.37 (d, J=2.7 Hz, 1H), 8.19 (q, J=0.7 Hz, 0.3??/Hz, 1H).

Step D:

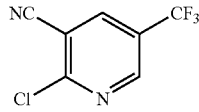

To a mixture of phosphorous oxychloride (13.4 mL, 144 mmol) and quinoline (8.7 mL, 73.4 mmol) was added the product from Step C (24.6 g, 131 mmol) and the resulting mixture was refluxed for 3 hours. The reaction was cooled to 100° C. before water (70 mL) was slowly added. The mixture was further cooled to room temperature and neutralized carefully with saturated NaHCO₃ solution. The aqueous layer was extracted with ethyl acetate (3×) and the organic layers were combined, dried over MgSO₄, filtered, and evaporated in vacuo. The crude product was purified by flash chromatography to afford (23.5 g, 87.0%) of the desired compound. ¹H NMR (500 MHz, CDCl₃) δ 8.88 (d, J=2.0 Hz, 1H), 8.26 (d, J=2.5 Hz, 1H).

Step E:

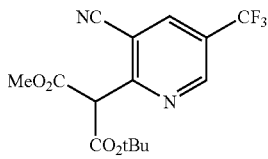

To a suspension of NaH (7.8 g, 200 mmol) in THF (100 mL) under nitrogen was added dropwise a solution of tert-butyl methyl malonate (20 mL, 120 mmol) in anhydrous THF (100 mL) via syringe. The reaction mixture was stirred for 0.5 h before a solution of the intermediate prepared in Step D (20.1 g, 97.6 mmol) in THF (200 mL) was added slowly via syringe. The reaction was stirred at room temperature overnight, then quenched with a saturated solution of NH₄Cl. The organic layer was separated and the aqueous layer extracted with ethyl acetate (3×). The combined organic layers were washed with water (3×), dried over Na₂SO₄, filtered, and evaporated in vacuo. Flash chromatography afforded 31.76 g (94.6%) of the pure desired product. 1H NMR (500 MHz, CDCl3) δ 9.03 (d, J=1.5 Hz, 1H), 8.25 (d, J=2.0 Hz, 1H), 5.25 (s, 1H), 3.86 (s, 3H), 1.52 (s, 9H).

Step F:

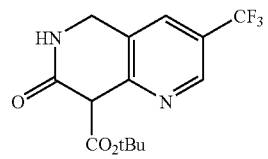

A suspension of Raney Ni (1 g) and the product from Step E (18.2 g, 52.9 mmol) in ethanol (130 mL) was placed on a Parr Apparatus and hydrogenated at 40 psi overnight. The suspension was filtered through celite and the filtrate evaporated in vacuo to afford 16.35 g (97.8%) of crude product. ¹H NMR (500 MHz, CDCl₃) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

Step G:

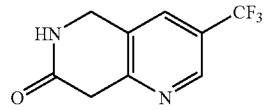

To the mixture of the product from Step F (16 g, 51 mmol) in DCM (60 mL) was added TFA (30 mL) and the resulting mixture stirred at room temperature for 0.5 h. The solution was evaporated under reduced pressure and the residue was dissolved in DCM. The mixture was neutralized by slow addition of a solution of saturated sodium bicarbonate and the organic layer removed. The aqueous was extracted with DCM (4×) and then all organic layers were combined, dried over Na₂SO₄, filtered, and evaporated in vacuo to afford 10.42 g (95.2%) of the desired product. ¹H NMR (400 MHz, CDCl₃) δ 8.81 (s, 1H), 7.78 (s, 1H), 7.30 (s, 1H), 4.63 (s, 2H), 3.90 (s, 2H).

Step H:

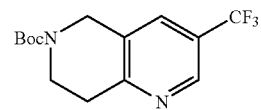

To a solution of the product from Step G (18.0 g, 83.3 mmol) in THF (50 mL) was added 1.0 M Borane in THF (417 mL, 420 mmol) and the resulting solution stirred at room temperature overnight. The solution was evaporated under reduced pressure and then the residue was treated with 1% HCl/MeOH solution in which the resulting mixture was heated at 50° C. overnight to breakdown the borane complex. Treatment with acidic methanol was repeated twice to insure that the borane complex was eliminated. The crude product from this reaction was then immediately used for the next reaction.

A solution of crude product described immediately above (83.3 mmol, assuming 100% conversion) and DIEA (43 mL, 250 mmol) in DCM was treated with di-tert-butyl dicarbonate (36.4 g, 167 mmol) and the resulting mixture stirred at room temperature overnight. The solution was washed with saturated sodium bicarbonate solution, water, and brine. The aqueous layers were combined and back-washed with DCM (2×). The combined organic layers were then dried over Na₂SO₄, filtered, and evaporated to dryness. The crude product was purified by flash chromatography and MPLC to afford (11.89 g, 47.2% for last two steps) as a yellow solid. ¹H NMR (500 MHz, CDCl₃) δ 8.69 (s, 1H), 7.66 (s, 1H), 4.67 (s, 2H), 3.79 (t, J=6.0 Hz, 2H), 3.08 (t, J=5.5 Hz, 2H), 1.51 (s, 9H).

Step I:

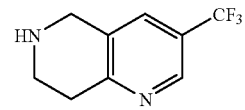

The product described in Step H (11.89 g) was treated with a solution of 4 M HCl in dioxane. The solution was stirred at room temperature for 2 hours and then evaporated in vacuo to afford Intermediate 2 (10.85 g, 99%) as a yellow powder. LC-MS for $C_9H_{10}F_3N_2[M^+H^+]$ calculated 202.07, found 203.0.

INTERMEDIATE 3

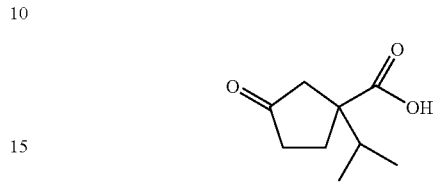

Step A:

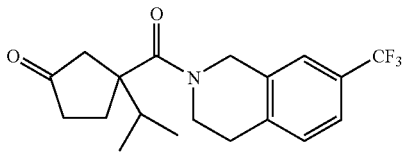

A solution of methyl-3-oxocyclopentane-carboxylate (20 g, 160 mmol) and trimethyl orthoformate (85 mL, 780 mmol) in methanol was treated with a catalytic amount of p-toluene-sulfonic acid (3.00 g, 15.6 mmol) and the resulting solution was stirred for 4 h at room temperature. The solvent was evaporated under reduced pressure and the residue was then dissolved in ether (600 mL). The solution was washed with saturated sodium bicarbonate (2×200 mL), water (150 mL), brine (200 mL), dried over anhydrous sodium sulfate, filtered, and the solvent evaporated as before. Purification by flash column chromatography (eluant: 25% ether/pentane) afforded 21.52 g (73%) of the desired product as a clear oil. $^1$H NMR (500 MHz, CDCl$_3$) δ 3.68 (s, 3H), 3.21 (d, J=9.9 Hz, 6H), 2.89 (p, J=8.5 Hz, 1H), 2.14-2.05 (m, 2H), 2.02-1.80 (m, 4H).

Step B:

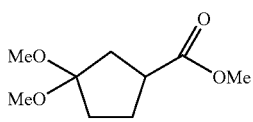

A flame dried 500 mL round bottom flask was charged with 150 mL of dry THF, and then, set under nitrogen and cooled to −78° C. using an acetone/dry ice bath. Diisopropylamine (19.2 mL, 137 mmol) was added to the cooled solvent via syringe followed by the slow addition of 2.5M n-butyllithium in hexane (55 mL, 140 mmol). After 5 minutes stirring, the methyl ketal described in Step A, Intermediate 3 (21.52 g, 114.4 mmol) in 50 mL of THF was added dropwise via syringe and the resulting mixture stirred at −78° C. for 2 hours. 2-Iodopropane (34.3 mL, 343 mmol) was then added dropwise via syringe and the resulting mixture was stirred overnight allowing to warm slowly to room temperature. The reaction was quenched with a solution of 10% citric acid and the organics separated. The aqueous layer was extracted with ether (3×150 mL) and all the organics combined, dried over anhydrous sodium sulfate, filtered, and evaporated under reduced pressure. The crude product was purified by flash column chromatography using an eluant of 20% ether/pentane to afford 16.74 g (64%) of the desired product. $^1$H NMR (400 MHz, CDCl$_3$) δ 3.69 (s, 3H), 3.18 (d, J=20.5 Hz, 6H), 2.57 (d, J=13.9 Hz, 1H), 2.29-2.20 (m, 1H), 1.90 (p, J=6.8 Hz, 1H), 1.88-1.80 (m, 2H), 1.69-1.61 (m, 2H), 0.89 (dd, J=11.9 Hz, 6.8 Hz, 6H).

Step C:

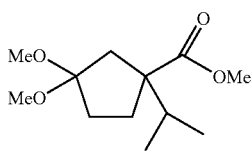

A solution of the ester (described in Step B, Intermediate 3, 16.7 g, 72.7 mmol) in ethanol (30 mL) was treated with 5 M NaOH (55 mL) and the resulting mixture heated to reflux for three days. The mixture was then cooled to room temperature and acidified with concentrated hydrochloric acid. The organic solvent was evaporated under reduced pressure and the aqueous layer was then extracted with DCM (5×100 mL). The organic extracts were combined, dried over anhydrous magnesium sulfate, filtered, and evaporated in vacuo to yield the crude 3-oxocyclopentane carboxylic acid (11.07 g, 90%) as a yellow oil. $^1$H NMR (500 MHz, CDCl$_3$) δ 2.70 (d, J=18.1 Hz, 1H), 2.44-2.39 (m, 1H), 2.30-2.15 (m, 2H), 2.14 (dd, J=18.1, 1.0 Hz, 1H), 2.06 (p, J=6.9 Hz, 1H), 1.98 (m, 1H), 0.98 (dd, J=11.4, 6.9 Hz, 6H).

Step D:

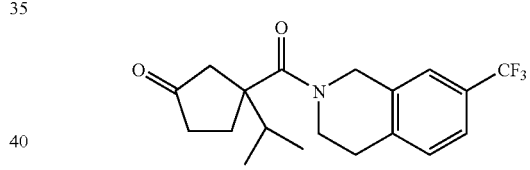

Procedure A:

To a solution of acid (described in Step C, Intermediate 3, 2.00 g, 11.8 mmol) in DCM (50 mL) was added oxalyl chloride (1.54 mL, 17.6 mmol) followed by 2 drops of DMF. The solution was stirred at room temperature for 80 minutes and then evaporated under reduced pressure. The residue was dissolved in DCM (2 mL) and added via syringe to a prepared solution of Intermediate 1 (2.36 g, 11.8 mmol) and triethylamine (2.13 mL, 15.3 mmol) in DCM (40 mL). The resulting mixture was stirred at room temperature for 18 hours and then quenched with water (25 mL). The organics were separated, washed with 1 N HCl, saturated sodium bicarbonate, and brine, dried over anhydrous magnesium sulfate, filtered, and evaporated. The crude product was purified by MPLC using an eluant of 60% ethyl acetate/hexane to afford Intermediate 3 (3.18 g, 77%). $^1$H NMR (500 MHz, CDCl$_3$) δ 7.46 (d, J=7.3 Hz, 1H), 7.39 (s, 1H), 7.29 (d, J=7.7 Hz, 1H), 4.81 (m, 2H), 3.93 (m, 1H), 3.82 (m, 1H), 2.94 (m, 3H), 2.54 (m, 1H), 2.43 (d, J=8.5 Hz, 1H), 2.32 (m, 2H), 2.26 (p, J=6.6 Hz, 1H), 2.16 (m, 1H), 0.93 (dd, J=19.7 Hz, 6.8 Hz, 6H). LC-MS for $C_{19}H_{23}F_3NO_2$ calculated 353.16, found [M+H$^+$] 354.25.

Procedure B:

A mixture of the acid prepared in Step C, Intermediate 3 (1.0 g, 5.9 mmol), Intermediate 1 (1.18 g, 5.88 mmol), DMAP (71 mg, 0.59 mmol), and N,N-diisopropyl ethylamine (1.02 mL, 5.88 mmol) in dichloromethane (20 mL) was treated with 1-[3-(dimethylamino)propyl]-3-ethylcarbodiimide hydrochloride (EDC, 2.25 g, 11.7 mmol) and stirred at room temperature overnight. The reaction mixture was diluted with dichloromethane (30 mL), washed with water (2×20 mL), brine (1×30 mL), dried over anhydrous sodium sulfate and the solvent was evaporated. The pure compound was obtained by MPLC purification (eluant 60% ethyl acetate/hexane), 1.08 g (52%). LC-MS for $C_{19}H_{23}F_3NO_2$ calculated 353.16, found [M+H$^+$] 354.25.

INTERMEDIATE 4

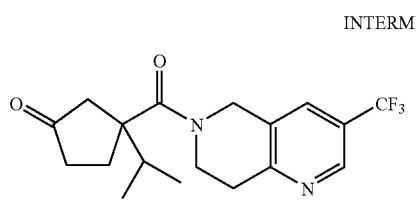

To a solution of acid (described in Step C, Intermediate 3, 540 mg, 3.20 mmol) in DCM (50 mL) was added oxalyl chloride (0.834 mL, 9.60 mmol) followed by 2 drops of DMF. The solution was stirred at room temperature for 80 minutes and then evaporated under reduced pressure. The residue was dissolved in DCM (2 mL) and added via syringe to a prepared solution of Intermediate 2 (880 mg, 3.20 mmol) and triethylamine (0.820 mL, 6.50 mmol) in DCM (20 mL). The resulting mixture was stirred at room temperature for 18 hours and then quenched with water (25 mL). The organics were separated, washed with saturated sodium bicarbonate and brine, dried over anhydrous sodium sulfate, filtered, and evaporated. The crude product was purified by MPLC using a step-wise gradient eluant of 0-70% ethyl acetate/hexane to afford Intermediate 2 (720 mg, 64%). ESI-MS calculated for C18H21F3N2O2: 354.16; found 355 (M+H).

INTERMEDIATE 5

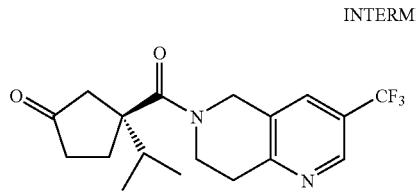

Resolution of Intermediate 4 to its individual enantiomers was accomplished by chiral separation using HPLC equipped with a Preparative ChiralPak AD column. The separation was completed by injecting 100 mg/run and using an eluant of 25% isopropanol and 75% heptane with a flow rate of 9 mL/min.

INTERMEDIATE 6

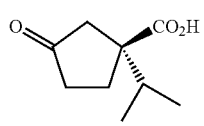

Procedure A:

Step A:

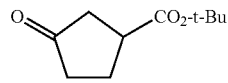

$H_2SO_4$ (conc., 15.3 g, 8.30 mL, 156 mmol) was added dropwise to a vigorously stirred suspension of $MgSO_4$ (75 g, 620 mmol) in DCM (650 mL). The mixture was stirred for 0.5 h, then known cyclopentanone-3-carboxylate (20.0 g, 156 mmol) was added, followed by t-butanol (58 g, 780 mmol). The reaction vessel was tightly sealed and the mixture was stirred overnight at room temperature. The next morning another 30 mL of t-butanol was added. Again the reaction vessel was tightly sealed, and the reaction mixture was stirred over the weekend. The reaction mixture was then filtered through celite. The filtrate was washed with 2 N NaOH. The aqueous layer was back-washed with DCM. The organic layers were combined, washed with water, then brine, dried over anhydrous $MgSO_4$, filtered, and concentrated to afford 19.9 g (69%) of tert-butyl 3-oxocyclopentanecarboxylate. The reaction progress was monitored by TLC using 50% ethyl acetate/hexane and staining with anisaldehyde stain (SM and product stain purple). $^1$H NMR (500 MHz, CDCl$_3$): 3.02 (p, J=7.8 Hz, 1H), 2.05-2.50 (m, 6H), 1.45 (s, 9H). $^{13}$C NMR (125 MHz, CDCl$_3$): 217.00, 173.47, 80.99, 41.88, 41.14, 27.94, 26.57.

Step B:

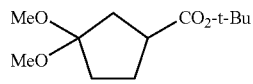

To a solution of tert-butyl 3-oxocyclopentanecarboxylate (19.8 g, 107 mmol) in 1:1 DCM/methanol (150 mL) was added trimethylorthoformate (46.8 mL, 428 mmol), followed by TsOH.H$_2$O (~0.5 g). The reaction mixture was stirred at room temperature for 2 h. Then more TsOH.H$_2$O (~0.25 g) was added and the reaction mixture was stirred overnight. The reaction mixture was concentrated at room temperature and the resulting residue was dissolved in ether and washed with saturated NaHCO$_3$ solution, then with brine. The ethereal layer was dried over anhydrous MgSO$_4$, filtered, and concentrated. Purification by flash chromatography (silica, 15% ethyl acetate/hexane) gave 22.2 g (90%) of tert-butyl 3,3-dimethoxycyclopentanecarboxylate. $^1$H NMR (500 MHz, CDCl$_3$): 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): 174.9, 111.2, 80.3, 67.8, 49.2, 42.5, 37.4, 33.8, 28.3, 22.0.

Step C:

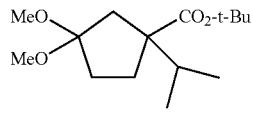

To a cooled (−78° C.) solution of LDA (1.5 M in cyclohexane, 41 mL, 61 mmol) in THF (150 mL) was added dropwise over 10 min tert-butyl 3,3-dimethoxycyclopentanecarboxylate (9.37 g, 40.7 mmol) in 25 mL of THF. The resulting mixture was stirred at −78° C. for 30 min, then was treated dropwise with 2-iodopropane (16.3 mL, 163 mmol). After stirring for an additional 10 min, the reaction mixture was permitted to warm to room temperature. After stirring overnight, the reaction mixture was diluted with ether and washed with brine. The ethereal layer was dried over anhydrous MgSO$_4$, filtered, and concentrated. After storing the crude product under vacuum overnight, it was purified by MPLC (silica, 20% ethyl acetate/hexane) to give 8.32 g of tert-butyl 1-isopropyl-3,3-dimethoxycyclopentanecarboxylate (75%). $^1$H NMR (500 MHz, CDCl$_3$) δ 3.21 (s, 3H), 3.18 (s, 3H), 2.56 (app d, J=14 Hz, 1H), 2.26 (m, 1H), 1.78-1.89 (m, 3

Step D:

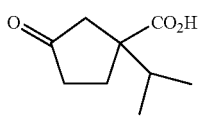

tert-Butyl 1-isopropyl-3,3-dimethoxycyclopentanecarboxylate (8.32 g, 30.5 mmol) was dissolved in 4 N anhydrous HCl in dioxane (50 mL) and water (10 mL) was added. The reaction mixture was stirred at room temperature overnight, then was concentrated. The residue was dissolved in DCM, dried over anhydrous MgSO$_4$, filtered, and concentrated to give 5.44 g of 1-isopropyl-3-oxocyclopentanecarboxylic acid (used without purification). $^1$H NMR (500 MHz, CDCl$_3$) δ 2.70 (d, J=18.1 Hz, 1H), 2.44-2.39 (m, 1H), 2.30-2.15 (m, 2H), 2.14 (dd, J=18.1, 1.0 Hz, 1H), 2.06 (p, J=6.9 Hz, 1H), 1.98 (m, 1H), 0.98 (dd, J=11.4, 6.9 Hz, 6H).

Step E:

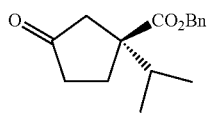

A cooled (0° C.) solution of 1-isopropyl-3-oxocyclopentanecarboxylic acid (5.44 g, 32.0 mmol) in DCM (75 mL) was treated with oxalyl chloride (8.36 mL, 95.9 mmol), followed by 3 drops of DMF. The reaction mixture was permitted to warm to room temperature and stir for 1.75 h. The reaction mixture was then concentrated and stored under vacuum for 30 min. The resulting acid chloride was dissolved in DCM (75 mL), cooled to 0° C., and treated with benzyl alcohol (8.28 mL, 80.0 mmol), followed by triethyl amine (8.92 mL, 64.0 mmol, dropwise). Then approximately 100 mg of DMAP was added and the reaction mixture was warmed to room temperature and stirred for 2 h. The reaction mixture was diluted with DCM and washed with 1 N HCl solution, saturated NaHCO$_3$ solution, and brine. The organic layer was dried over anhydrous MgSO$_4$, filtered, and concentrated. Purification by MPLC (silica, 50% ethyl acetate/hexane) gave 6.11 g (73%) of benzyl 1-isopropyl-3-oxocyclopentanecarboxylate. $^1$H NMR (CDCl$_3$, 500 MHz): δ 7.36 (m, 5H), 5.17 (d, J=2.5 Hz, 2H), 2.85 (d, J=18.5 Hz, 1H), 2.48 (m, 1H), 2.29 (dd, J=10.0, 3.0 Hz, 1H), 1.98-2.23 (m, 3H), 1.93 (m, 1H), 0.95 (m, 6H).

Resolution of the racemic product was accomplished by chiral HPLC using a chiralcel OD column, and eluting with 15% 2-propanol/hexane (100 mg/injection; was accomplished using a programmed Gilson HPLC system). 2.11 g of the desired faster eluting isomer, benzyl (1S)-1-isopropyl-3-oxocyclopentanecarboxylate, were obtained.

Step F:

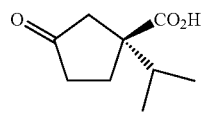

Benzyl (1S)-1-isopropyl-3-oxocyclopentanecarboxylate (1.27 g, 4.88 mmol) was combined with Pd/C (10% Degussa, 500 mg) in 20 mL of methanol and stirred under a hydrogen atmosphere (balloon) for 2 h. The reaction had only proceeded part way (~30% conversion) so the reaction mixture was filtered, another portion of Pd/C (500 mg) was added, and the mixture was stirred under a hydrogen atmosphere for 5 h. Since the reaction had now gone to completion, the reaction mixture was filtered through celite and concentrated to afford 704 mg of (1S)-1-isopropyl-3-oxocyclopentanecarboxylic acid that did not require further purification. Note that the large quantities of catalyst were used because the ester obtained after chiral separation must have been poisoned by an impurity. This was unique to this particular sample. Normally much smaller quantities of catalyst are used. $^1$H NMR was identical to that of the racemic acid above (Step D).

INTERMEDIATE 7

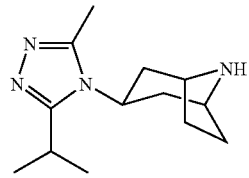

Intermediate 7 is prepared as described in Perros, M, et. al. US 2002/0013337 A1.

INTERMEDIATE 8

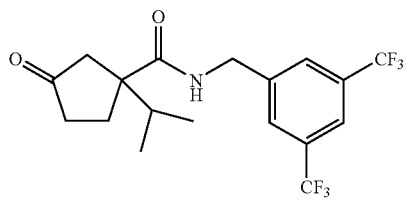

Step A:

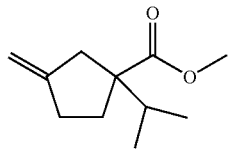

A solution of diisopropylamine (530 μL, 3.76 mmol) in tetrahydrofuran (15 mL) was cooled to −78° C. and nBuLi (1.50 mL, 3.76 mmol, 2.5 M sol. in hexanes) was added via syringe. The neat methyl 3-methylenecyclopentane carboxylate was added via syringe 15 minutes later, and the stirring at −78° C. was continued for another 30 minutes. Isopropyl bromide (921 μL, 9.81 mmol) was injected, and the resulting solution was allowed to warm up to +5° C. overnight and stirred at room temperature for additional 8 hrs. The reaction was quenched with a sat. solution of ammonium chloride (50 mL) and extracted with diethyl ether (2×50 mL). The combined organic extracts were washed with water (2×40 mL), brine (1×40 mL), dried (anh. magnesium sulfate) and the solvent was evaporated under reduced pressure (80 torr) to yield 340 mg (57%) of product with satisfactory purity. $^1$H NMR (500 MHz, CDCl$_3$) 4.86 (bs, 1H), 4.81 (bs, 1H), 3.67 (s, 3H), 2.87 (bd, 16.7 Hz, 1H), 2.29 (m, 3H), 1.90 (m, 1H), 1.60 (m, 1H), 1.34 (d, 6.2 Hz, 1H), 0.93 (d, 3.7 Hz, 3H), 0.91 (d, 3.7 Hz, 3H).

Step B:

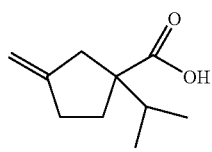

A solution of the methyl 3-methylene-1-isopropylcyclopentanecarboxylate (Step A) in a mixture of dioxane (4 mL) and water (4 mL) containing 1.114 g (26.56 mmol) of lithium hydroxide monohydrate was homogenized with methanol, and stirred at 80° C. for 48 hrs. The solvent was removed in vacuo, the residue was dissolved in water and the non-acidic components were extracted with diethyl ether (3×30 mL), combined ethers were back-washed with water (1×30 mL). The combined aqueous phases were acidified with 2N HCl and extracted with chloroform (6×30 mL), dried (anhydrous magnesium sulfate) and evaporated to dryness to leave 1.25 g of crude acid. It was used in the next reaction step without any further purification.

Step C:

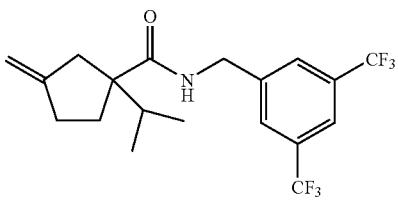

The solution of 3-methylene-1-isopropylcyclopentanecarboxylic acid from the previous step (1.25 g, 7.44 mmol) 3,5-bis(trifluoromethyl)benzylamine hydrochloride (2.08 g, 7.44 mmol), dimethylaminopyridine (111.0 mg, 0.91 mmol) and diisopropylethylamine (1.29 mL, 7.44 mmol) and 1-[3-(dimethylamino)propyl]-3-ethylcarbodiimide hydrochloride (EDC, 2.85 g, 14.9 mmol) in dichloromethane (50 mL) was stirred at room temperature for 24 hrs. The reaction mixture was diluted with dichloromethane (100 mL) and washed with water (3×50 mL), brine (1×50 mL), dried (anhydrous sodium sulfate) and the solvent was evaporated under reduced pressure. The crude product was purified via mplc (Lobar Fertigsaule, LiChroprep, 40-63 μm, ethyl acetate/hexanes (1:4)) yielding 910 mg (31%) of pure product. $^1$H NMR (500 MHz, CDCl$_3$): 7.76 (s, 1H), 7.70 (s, 2H), 6.20 (bs, 1H), 4.95 (bs, 1H), 4.88 (bs, 1H), 4.65 (dd, J=15.70, 6.40 Hz, 1H), 4.50 (dd, J=15.50, 5.70 Hz, 1H), 2.68 (bd, J=16.20 Hz, 1H), 2.50 to 2.10 (bm, 4H), 1.96 (h, J=6.9 Hz, 1H), 1.74 (m, 1H), 0.87 (d, J=6.9 Hz, 3H), 0.85 (d, J=7.3 Hz, 3H).

Step D:

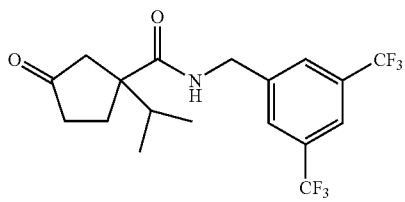

A solution of 3,5-bis(trifluoromethyl)benzyl 3-methylene-1-isopropylcyclopentane-carboxamide (910 mg, 2.31 mmol) in dichloromethane (50 mL) was cooled to −78° C. and a stream of ozone was passed through until the permanent blue color indicated complete consumption of the olefin. The excess ozone was purged with a stream of nitrogen, and triphenylphosphine (729 mg, 2.78 mmol) was added. The cooling bath was removed, and the reaction mixture was allowed to stir at ambient temperature overnight. The solvent was removed in vacuo, the residue was purified by column chromatography (silica gel, ethyl acetate:hexane/1:2) to give 760.7 mg (83%) of the desired product. $^1$H NMR (500 MHz, CDCl$_3$): 7.81 (s, 1H), 7.74 (s, 2H), 6.16 (bs, 1H), 6.61 (m, 2H), 2.78 (bd, J=18.07 Hz, 1H), 2.40 to 2.20 (bm, 4H), 2.08-1.98 (m, 2H), 0.99 (d, J=6.86 Hz, 3H), 0.97 (d, J=6.87 Hz, 3H).

INTERMEDIATE 9

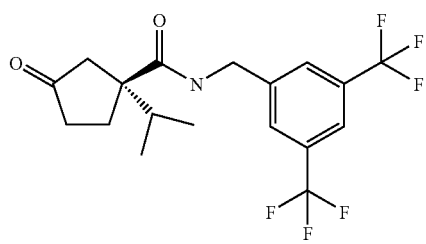

Intermediate 9 was synthesized according to the procedure described in Intermediate 8, Step C except that 3-methylene-1-isopropylcyclopentanecarboxylic acid was replaced with Intermediate 6.

INTERMEDIATE 10

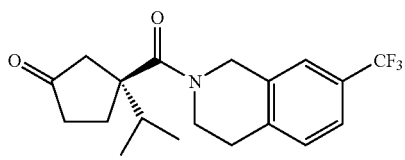

Intermediate 6 (100 mg, 0.588 mmol) was dissolved in DCM (20 mL) and treated sequentially with oxalyl chloride (153 μL, 1.76 mmol) and DMF (1 drop). The resulting solution was stirred at room temperature for 2 h, before being concentrated to dryness and dried under high vacuum for 30 min. The resulting residue was dissolved in DCM (5 mL) and added dropwise to a stirred solution of Intermediate 1 (177 mg, 0.882 mmol) in DCM (5 mL) and triethylamine (5 mL). The resulting reaction mixture was stirred at room temperature overnight, before being diluted with DCM and washed with bicarb, 1 N aqueous HCl, and brine. The organic layer was dried over MgSO₄, filtered, and concentrated under reduced pressure to give 230 mg of the desired product, which was used directly without further purification.

EXAMPLE 1

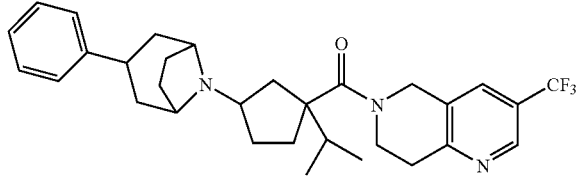

Step A:

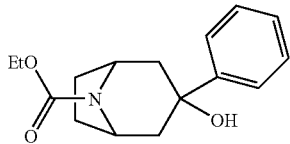

To a mixture of N-carbethoxy-4-tropinone (1 g, 5 mmol) and tetrahydrofuran (20 mL) was added phenyl magnesium bromide (1.38 g, 7.61 mmol), and the reaction stirred at room temperature for 5 hours. The mixture was quenched with water and concentrated in vacuo to yield the desired product (1.7 g, 100%). Results were verified by LCMS and HPLC (retention time=7.307 min). The crude product was used in the next step.

Step B:

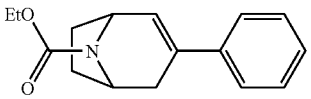

To a solution of the product from Step A (1.7 g, 6.2 mmol) in toluene (20 mL) was added p-toluenesulfonic acid monohydrate (25 mg, 0.13 mmol), and the mixture was refluxed at 120° C. for 2 hours and concentrated in vacuo to yield the desired product (1.4 g, 100%). Results were verified via HPLC (retention time=8.427 min). The crude product was used in the following step.

Step C:

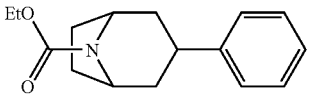

To a solution of the product from Step B (1.4 g, 5.44 mmol) and methanol (40 mL) was added palladium/carbon (140 mg), and the mixture was hydrogenated at 50 psi overnight. The mixture was filtered, concentrated in vacuo, and purified through MPLC (0-50% ethyl acetate/hexanes) to yield the desired product (500 mg, 36%). Results were verified via HPLC (retention time=9.365 min)

Step D:

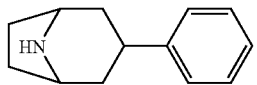

To a solution of the product from Step C (500 mg, 1.93 mmol) in ethylene glycol (50 mL) was added potassium hydroxide (2.16 g, 38.6 mmol) and hydrazine hydrate (580 mg, 11.6 mmol), and the mixture was heated at 145° C. for 3 hours. The mixture was extracted with ether, washed with water, filtered through celite with methanol/methylene chloride (5/95) and concentrated in vacuo to give the desired product (400 mg, 100%). Results were verified via LCMS. The crude product was used in the next step.

Step E:

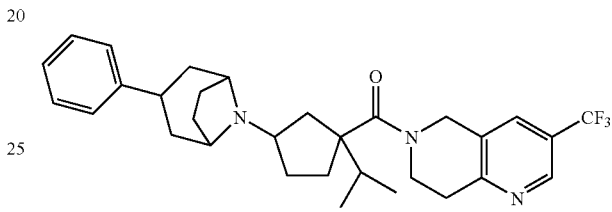

To a solution of the product from Step D (50 mg, 0.27 mmol) in methylene chloride anhydrous (15 mL) was added Intermediate 4 (95 mg, 0.27 mmol). After adding molecular sieves (50 mg), sodium triacetoxyborohydride (284 mg, 1.34 mmol) was added and the mixture stirred overnight. The mixture was extracted with methylene chloride, washed with sodium bicarbonate, dried under sodium sulfate and concentrated in vacuo. The crude product was purified on preparation plates (10/89/1, methanol/methylene chloride/ammonium hydroxide); 4 N HCl in dioxane was added and the solution was concentrated in vacuo to yield Example 1 (55 mg, 74%). LC-MS: MW calculated 525.30, found 526.6.

EXAMPLE 2

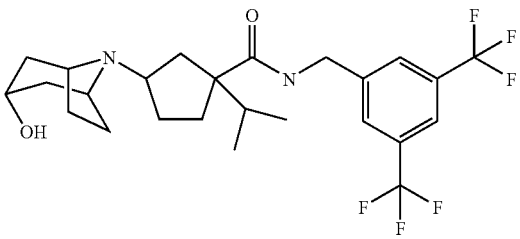

Step A:

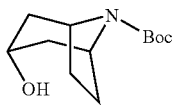

A solution of N-Boc-nortropinone (1.97 g, 9.00 mmol) in THF (20 mL) was cooled and stirred at −78° C. under nitrogen protection. A 1.0 M solution of L-Selectride (10 mL, 10 mmol) in THF was added dropwise. The reaction mixture was then stirred for 2 h at RT, quenched with sat. aq. Ammonium chloride, extracted with ether twice. The ether solution was dried over sodium sulfate, filtered, evaporated. The residue was purified on FC (Silica gel, eluted with 10% ethyl acetate/hexane) to give a white solid (1.4 g). LC-MS: 228. Calc. $C_{12}H_{21}NO_3$: 227.

Step B:

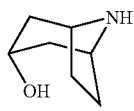

N-Boc-nortropinol (Step A) (0.6 g) was treated with 5 mL of 4 N HCl/dioxane for 1 h, evaporated, dried to give a white solid which was used for further reaction without purification.

Step C:

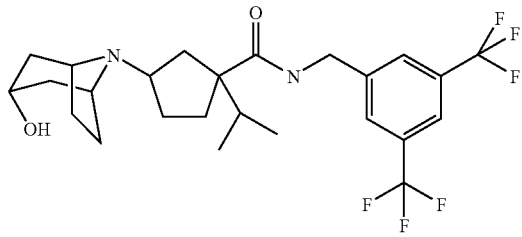

A mixture of the above nortropinol hydrochloride (from Step B) (325 mg, 2.00 mmol), the product from Intermediate 8 (200 mg, 0.5 mmol), molecular sieves (4 Å, 200 mg), DIEA (390 mg, 3.0 mmol) and sodium triacetoxyboride (0.64 g, 3.0 mmol) in dichloromethane (5 mL) was stirred overnight. The reaction was mixed with aq. Sat. sodium carbonate (20 mL), heated at 60° C. for 30 min, extracted with dichloromethane (2×20 mL). The dichloromethane solution was dried over sodium sulfate, filtered and evaporated. The residue was loaded on preparative TLC (1000 micron), developed with 10% [1/9 aq. $NH_4OH$/MeOH]/DCM. The desired product was obtained as a white solid (120 mg). LC-MS: 507Calc. $C_{25}H_{32}F_6N_2O_2$: 506.

EXAMPLE 3

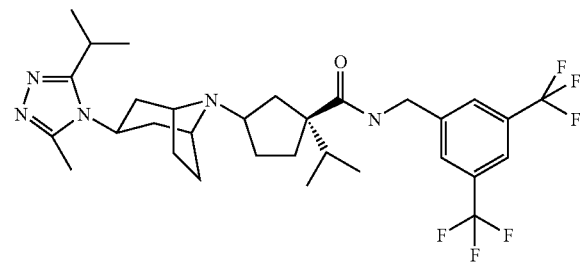

Example 3 is prepared according to the procedure described in Example 2, Step C except that Intermediate 9 is used in place of the product from Example 2, Step B. The individual stereoisomers are separated by chiral chromatography.

EXAMPLE 4

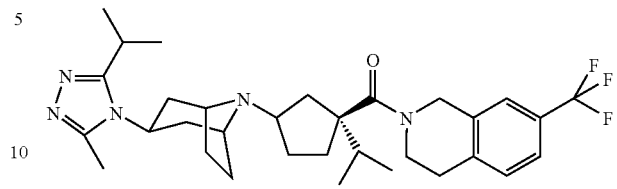

Example 4 is prepared according to the procedure described in Example 2, Step C except that Intermediate 10 is used in place of the product from Example 2, Step B. The individual stereoisomers are separated by chiral chromatography.

EXAMPLE 5

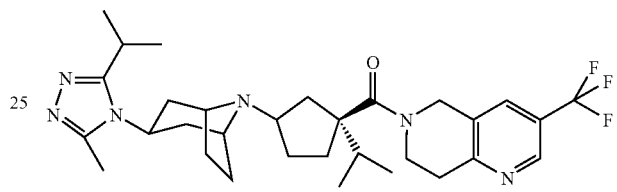

Example 5 is prepared according to the synthesis described in Example 2, Step C except that Intermediate 5 is used in place of the product from Example 2, Step B. The individual stereoisomers are separated by chiral chromatography.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

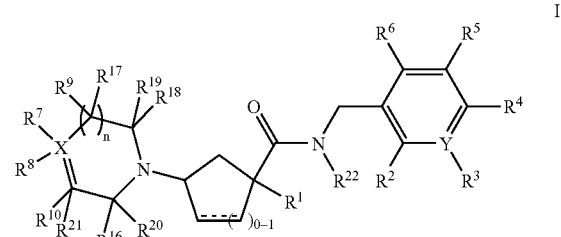

wherein:

X is C;

Y is N;

$R^1$ is selected from: hydrogen, —$SO_2R^{14}$, —$C_{0-3}$alkyl-S(O)$R^{14}$, —$SO_2NR^{12}R^{12}$, —$C_{1-6}$alkyl, —$C_{0-6}$alkyl-O—$C_{1-6}$alkyl, —$C_{0-6}$alkyl-S—$C_{1-6}$alkyl, —($C_{0-6}$alkyl)-($C_{3-7}$cycloalkyl)-($C_{0-6}$alkyl), hydroxy, heterocycle, —CN, —$NR^{12}R^{12}$, —$NR^{12}COR^{13}$, —$NR^{12}SO_2R^{14}$, —$COR^{11}$, —$CONR^{12}R^{12}$, and phenyl, where said alkyl and said cycloalkyl are unsubstituted or substituted with 1-7 substituents independently selected from: halo, hydroxy, —O—$C_{1-3}$alkyl, trifluoromethyl, $C_{1-3}$alkyl, —O—$C_{1-3}$alkyl, —$COR^{11}$, —$SO_2R^{14}$, —$NHCOCH_3$, —$NHSO_2CH_3$, -heterocycle, =O, and —CN, where said phenyl and said heterocycle are unsubstituted or substituted with 1-3 substituents independently selected from: halo, hydroxy, $C_{1-3}$alkyl, $C_{1-3}$alkoxy and trifluoromethyl;

$R^2$ is selected from: hydrogen, $C_{1-3}$alkyl unsubstituted or substituted with 1-3 fluoro, —O—$C_{1-3}$alkyl unsubstituted or substituted with 1-3 fluoro, hydroxy, chloro, fluoro, bromo, phenyl and heterocycle;

$R^3$ is oxygen or is absent;

$R^4$ is selected from: hydrogen, $C_{1-6}$alkyl, trifluoromethyl, trifluoromethoxy, chloro, fluoro, bromo, and phenyl;

$R^5$ is selected from: $C_{1-6}$alkyl unsubstituted or substituted with one or more substituents selected from 1-6 fluoro and hydroxyl, —O—$C_{1-6}$alkyl unsubstituted or substituted with 1-6 fluoro, —CO—$C_{1-6}$alkyl unsubstituted or substituted with 1-6 fluoro, —S—$C_{1-6}$alkyl unsubstituted or substituted with 1-6 fluoro, -pyridyl unsubstituted or substituted with one or more substituents selected from halo, trifluoromethyl, $C_{1-4}$alkyl and $COR^{11}$, fluoro, chloro, bromo, —$C_{4-6}$cycloalkyl, —O—$C_{4-6}$cycloalkyl, phenyl unsubstituted or substituted with one or more substituents selected from halo, trifluoromethyl, $C_{1-4}$alkyl and $COR^{11}$, —O-phenyl unsubstituted or substituted with one or more substituents selected from halo, trifluoromethyl, $C_{1-4}$alkyl and $COR^{11}$, —$C_{3-6}$cycloalkyl unsubstituted or substituted with 1-6 fluoro, —O—$C_{3-6}$cycloalkyl unsubstituted or substituted with 1-6 fluoro, -heterocycle, —CN and —$COR^{11}$;

$R^6$ is selected from: hydrogen, $C_{1-6}$alkyl, trifluoromethyl, fluoro, chloro and bromo;

$R^7$ is selected from: hydrogen, ($C_{0-6}$alkyl)-phenyl, ($C_{0-6}$alkyl)-heterocycle, ($C_{0-6}$alkyl)-$C_{3-7}$cycloalkyl, ($C_{0-6}$alkyl)-$COR^{11}$, ($C_{0-6}$alkyl)-(alkene)-$COR^{11}$, ($C_{0-6}$alkyl)-$SO_3H$, ($C_{0-6}$alkyl)-W—$C_{0-4}$alkyl, ($C_{0-6}$alkyl)-$CONR^{12}$-phenyl and ($C_{0-6}$alkyl)-$CONR^{15}$—V—$COR^{11}$, where V is selected from $C_{1-6}$alkyl and phenyl, where W is selected from: a single bond, —O—, —S—, —SO—, —$SO_2$—, —CO—, —$CO_2$—, —$CONR^{12}$— and —$NR^{12}$—, where said $C_{0-6}$alkyl is unsubstituted or substituted with 1-5 substituents independently selected from: halo, hydroxy, —$C_{0-6}$alkyl, —O—$C_{1-3}$alkyl, trifluoromethyl and —$C_{0-2}$alkyl-phenyl, where said alkene is unsubstituted or substituted with 1-3 substituents independently selected from: halo, trifluoromethyl, $C_{1-3}$alkyl, phenyl and heterocycle;

where said phenyl, heterocycle, cycloalkyl and $C_{0-4}$alkyl are independently unsubstituted or substituted with 1-5 substituents independently selected from: halo, trifluoromethyl, hydroxy, $C_{1-6}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle, or where said phenyl and heterocycle are fused to another heterocycle, which itself may be unsubstituted or substituted with 1-2 substituents independently selected from hydroxy, halo, —$COR^{11}$, and —$C_{1-4}$alkyl;

$R^8$ is selected from: hydrogen, hydroxy, $C_{1-6}$alkyl, $C_{1-6}$alkyl-hydroxy, —O—$C_{1-3}$alkyl, —$COR^{11}$, —$CONR^{12}R^{12}$ and —CN, or $R^8$ is nothing when a double bond joins the carbons to which $R^7$ and $R^{10}$ are attached;

or $R^7$ and $R^8$ are joined together to form a ring which is selected from: 1H-indene, 2,3-dihydro-1H-indene, 2,3-dihydro-benzofuran, 1,3-dihydro-isobenzofuran, 2,3-dihydro-benzothiofuran, 1,3-dihydro-isobenzothiofuran, 6H-cyclopenta[d]isoxazol-3-ol, cyclopentane and cyclohexane, where said ring is unsubstituted or substituted with 1-5 substituents independently selected from: halo, trifluoromethyl, hydroxy, $C_{1-3}$alkyl, —O—$C_{1-3}$alkyl, —$C_{0-3}$—$COR^{11}$, —CN, —$NR^{12}R^{12}$, —$CONR^{12}R^{12}$ and —$C_{0-3}$-heterocycle;

$R^9$ and $R^{10}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, =O when $R^9$ or $R^{10}$ is connected to the ring via a double bond and halo;

or $R^7$ and $R^9$, or $R^8$ and $R^{10}$, are joined together to form a ring which is phenyl or heterocycle, where said ring is unsubstituted or substituted with 1-7 substituents independently selected from: halo, trifluoromethyl, hydroxy, $C_{1-3}$alkyl, —O—$C_{1-3}$alkyl, —$COR^{11}$, —CN, —$NR^{12}R^{12}$ and —$CONR^{12}R^{12}$;

$R^{11}$ is independently selected from: hydroxy, hydrogen, $C_{1-6}$ alkyl, —O—$C_{1-6}$alkyl, benzyl, phenyl, $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{12}$ is selected from: hydrogen, $C_{1-6}$ alkyl, benzyl, phenyl and $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{13}$ is selected from: hydrogen, $C_{1-6}$ alkyl, —O—$C_{1-6}$alkyl, benzyl, phenyl and $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{14}$ is selected from: hydroxy, $C_{1-6}$ alkyl, —O—$C_{1-6}$alkyl, benzyl, phenyl and $C_{3-6}$ cycloalkyl, where said alkyl, phenyl, benzyl or cycloalkyl group is unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl and trifluoromethyl;

$R^{15}$ is hydrogen or $C_{1-4}$alkyl, or $R^{15}$ is joined via a 1-5 carbon tether to one of the carbons of V to form a ring;

$R^{17}$, $R^{19}$, $R^{20}$ and $R^{21}$ are independently selected from: hydrogen, hydroxy, $C_{1-6}$alkyl, $C_{1-6}$alkyl-$COR^{11}$, $C_{1-6}$alkyl-hydroxy, —O—$C_{1-3}$alkyl, trifluoromethyl and halo;

$R^{16}$ and $R^{18}$ together form a bridge consisting of —$C_{1-4}$alkyl-, —$C_{0-2}$alkyl-O—$C_{1-3}$alkyl- or —$C_{1-3}$alkyl-O—$C_{0-2}$alkyl-, where said alkyl is unsubstituted or substituted with 1-2 substituents independently selected from: oxy where the oxygen is joined to said bridge via a double bond, fluoro, hydroxy, methoxy, methyl and trifluoromethyl;

$R^{22}$ is selected from: hydrogen, phenyl, $C_{1-6}$alkyl which is substituted or unsubstituted with 1-6 substituents selected from: —$COR^{11}$, hydroxy, fluoro, chloro and —O—$C_{1-3}$alkyl;

or $R^2$ and $R^{22}$ together are a linker, forming a heterocycle ring, said linker selected from (with the left side of the linker being bonded to the amide nitrogen at $R^{22}$): —$CH_2(CR^{23}R^{23})_{1-3}$—, —$CH_2$—$NR^{24}$—, —$NR^{12}$—$CR^{23}R^{23}$—, —$CH_2O$—, —$CH_2SO_2$—, —$CH_2SO$—, —$CH_2S$—, —$CR^{23}R^{23}$—;

$R^{23}$ is independently selected from: hydrogen, $C_{1-3}$alkyl unsubstituted or substituted with 1-6 substituents independently selected from fluoro and hydroxy, $COR^{13}$, $SO_2R^{14}$, $SO_2NR^{12}R^{12}$, hydroxy, halo, —$NR^{12}R^{12}$, —$COR^{11}$, —$CONR^{12}R^{12}$, —$NR^{12}COR^{13}$, —$OCONR^{12}R^{12}$, —$NR^{12}CONR^{12}R^{12}$, -heterocycle, —CN, —$NR^{12}$—$SO_2$—$NR^{12}R^{12}$, —$NR^{12}$—$SO_2$—$R^{14}$, and —$SO_2$—$NR^{12}R^{12}$;

or one $R^{23}$ is =O and the other $R^{23}$ is absent;

where $R^{24}$ is selected from: hydrogen, $C_{1-3}$alkyl where said alkyl is unsubstituted or substituted with 1-6 substituents independently selected from fluoro and hydroxy, $COR^{13}$, $SO_2R^{14}$ and $SO_2NR^{12}R^{12}$;

n is selected from 0, 1 and 2;

the dashed line represents an optional bond;

and pharmaceutically acceptable salts thereof and individual diastereomers thereof.

2. The compound of claim 1 of the Formula Ia:

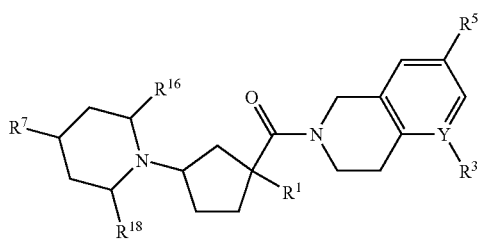

Ia and pharmaceutically acceptable salts thereof and individual diastereomers thereof.

3. The compound of claim 1 of the Formula Ib:

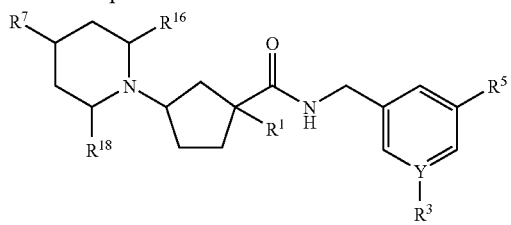

Ib and pharmaceutically acceptable salts thereof and individual diastereomers thereof.

4. The compound of claim 1 of the Formula Ic:

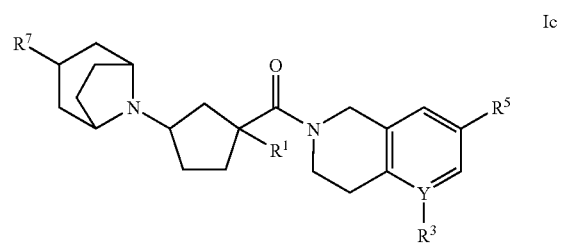

Ic and pharmaceutically acceptable salts thereof and individual diastereomers thereof.

5. The compound of claim 1 of the Formula Id:

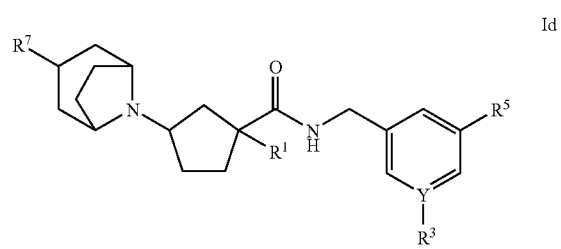

Id and pharmaceutically acceptable salts thereof and individual diastereomers thereof.

6. The compound of claim 1, wherein $R^1$ is $C_{1-6}$alkyl, unsubstituted or substituted with hydroxyl or 1-6 fluoro, and pharmaceutically acceptable salts thereof and individual diastereomers thereof.

7. The compound of claim 5, wherein $R^1$ is selected from: —$CH(CH_3)_2$, —$CH(OH)CH_3$ and —$CH_2CF_3$, and pharmaceutically acceptable salts thereof and individual diastereomers thereof.

8. The compound of claim 1, wherein $R^2$ is hydrogen, and pharmaceutically acceptable salts thereof and individual diastereomers thereof.

9. The compound of claim 1, wherein $R^2$ is connected to $R^{22}$ by —$CH_2$—$CH_2$—, and pharmaceutically acceptable salts thereof and individual diastereomers thereof.

10. The compound of claim 1, wherein $R^3$ is absent, and pharmaceutically acceptable salts thereof and individual diastereomers thereof.

11. The compound of claim 1, wherein $R^3$ is O, and pharmaceutically acceptable salts thereof and individual diastereomers thereof.

12. The compound of claim 1, wherein $R^4$ is hydrogen, and pharmaceutically acceptable salts thereof and individual diastereomers thereof.

13. The compound of claim 1, wherein $R^5$ is selected from: $C_{1-6}$alkyl substituted with 1-6 fluoro, —O—$C_{1-6}$alkyl substituted with 1-6 fluoro, chloro, bromo and phenyl, and pharmaceutically acceptable salts thereof and individual diastereomers thereof.

14. The compound of claim 12, wherein $R^5$ is trifluoromethyl, and pharmaceutically acceptable salts thereof and individual diastereomers thereof.

15. The compound of claim 1, wherein $R^6$ is hydrogen, and pharmaceutically acceptable salts thereof and individual diastereomers thereof.

16. The compound of claim 1, wherein $R^7$ is phenyl, heterocycle, $C_{3-7}$cycloalkyl, $C_{1-6}$alkyl, —$COR^{11}$ or —CONH—V—$COR^{11}$, where V is $C_{1-6}$alkyl or phenyl, where said phenyl, heterocycle, $C_{3-7}$cycloalkyl and $C_{1-6}$alkyl are unsubstituted or substituted with 1-5 substituents independently selected from: halo, trifluoromethyl, hydroxy, $C_{1-3}$alkyl, —O—$C_{1-3}$alkyl, —$COR^{11}$, —CN, -heterocycle and —$CONR^{12}R^{12}$, and pharmaceutically acceptable salts thereof and individual diastereomers thereof.

17. The compound of claim 1, wherein $R^7$ is phenyl, heterocycle, $C_{1-4}$alkyl, —$COR^{11}$, and —CONH—V—$COR^{11}$, where V is selected from $C_{1-6}$alkyl or phenyl, and where the phenyl, heterocycle, and $C_{1-4}$alkyl is unsubstituted or substituted with 1-3 substituents independently selected from: halo, hydroxy, $C_{1-3}$alkyl, —O—$C_{1-3}$alkyl, —$COR^{11}$ and -heterocycle, and pharmaceutically acceptable salts thereof and individual diastereomers thereof.

18. The compound of claim 1, wherein, $R^7$ is selected from:

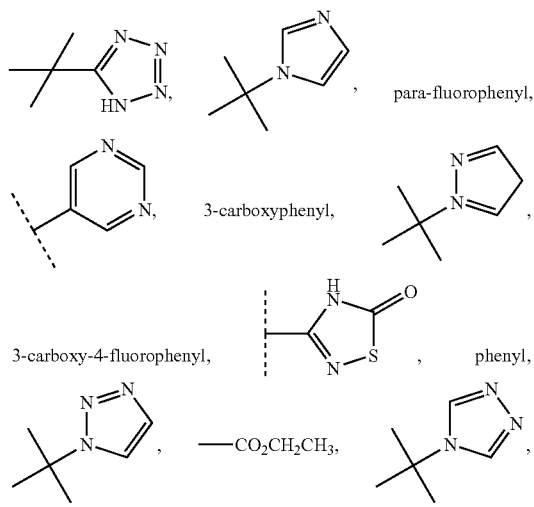

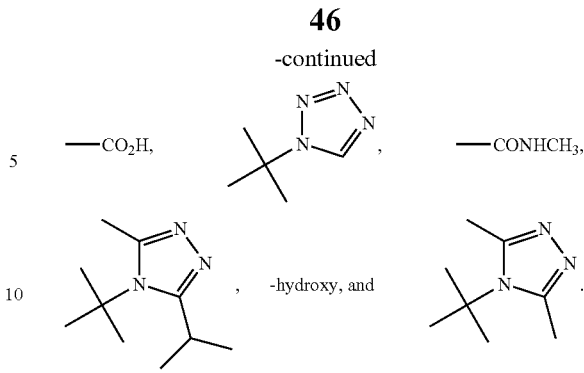

and pharmaceutically acceptable salts thereof and individual diastereomers thereof.

19. The compound of claim 1, wherein, $R^8$ is hydrogen, and pharmaceutically acceptable salts thereof and individual diastereomers thereof.

20. The compound of claim 1, wherein $R^9$ and $R^{10}$ are hydrogen, and pharmaceutically acceptable salts thereof and individual diastereomers thereof.

21. The compound of claim 1, wherein $R^{17}$ is hydrogen, and pharmaceutically acceptable salts thereof and individual diastereomers thereof.

22. The compound of claim 1, wherein $R^{16}$ and $R^{18}$ are joined by —$CH_2$—$CH_2$— to make a 5 membered heterocycle, and pharmaceutically acceptable salts thereof and individual diastereomers thereof.

23. The compound of claim 1, wherein one or more of $R^{19}$, $R^{20}$, $R^{21}$ and $R^{22}$ is hydrogen, and pharmaceutically acceptable salts thereof and individual diastereomers thereof.

24. The compound of claim 1, wherein n is 1, and pharmaceutically acceptable salts thereof and individual diastereomers thereof.

25. A compound selected from:

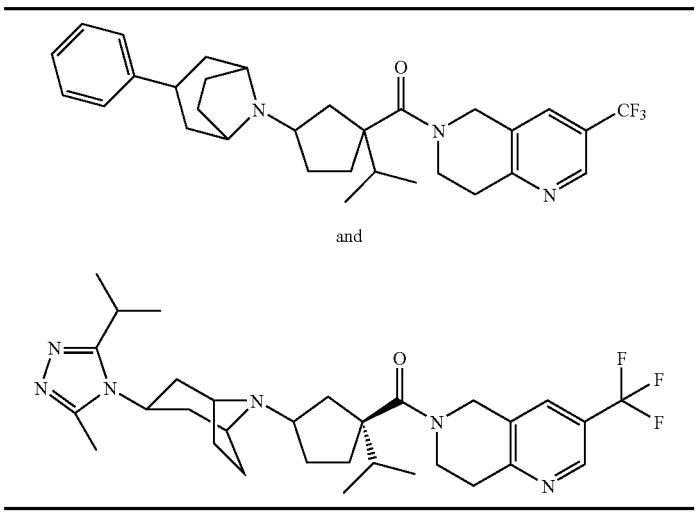

and pharmaceutically acceptable salts thereof and individual diastereomers thereof.

26. A pharmaceutical composition which comprises an inert carrier and a compound of claim 1.

* * * * *